United States Patent
Trudsoe et al.

(10) Patent No.: US 8,323,513 B2
(45) Date of Patent: Dec. 4, 2012

(54) DEWATERING BIOMASS MATERIAL COMPRISING POLYSACCHARIDE, METHOD FOR EXTRACTING POLYSACCHARIDE FROM BIOMASS MATERIAL, AND DEWATERED BIOMASS MATERIAL

(75) Inventors: Jens Eskil Trudsoe, Roskilde (DK); Helle Bech Olsen, Haslev (DK); Mogens Andersen, Støbe Egede (DK)

(73) Assignee: CP Kelco ApS (DK)

( * ) Notice: Subject to any disclaimer, the term of this patent is extended or adjusted under 35 U.S.C. 154(b) by 625 days.

(21) Appl. No.: 12/510,478

(22) Filed: Jul. 28, 2009

(65) Prior Publication Data

US 2011/0028426 A1    Feb. 3, 2011

(51) Int. Cl.
*A61K 31/715* (2006.01)
*C07H 1/06* (2006.01)
*C07G 1/00* (2011.01)
*A62D 3/40* (2007.01)

(52) U.S. Cl. .............. 210/770; 210/772; 127/2; 127/43; 426/615; 426/658; 536/123.1; 536/128

(58) Field of Classification Search ................ 127/2, 43; 210/770, 772; 426/615, 658; 536/123.1, 536/128
See application file for complete search history.

(56) References Cited

U.S. PATENT DOCUMENTS

| | | |
|---|---|---|
| 1,654,131 A | 12/1927 | Leo |
| 2,022,471 A | 11/1935 | Leo et al. |
| 2,727,033 A | 12/1955 | Norman et al. |
| 4,001,458 A | 1/1977 | Morolo |
| 4,119,435 A | 10/1978 | Nakao et al. |
| 4,435,437 A | 3/1984 | Ziegler |
| 4,451,489 A | 5/1984 | Beale et al. |
| 4,497,838 A | 2/1985 | Bonnell |
| 4,497,842 A | 2/1985 | Ehrlich et al. |
| 4,508,747 A | 4/1985 | Ziegler |
| 4,526,794 A | 7/1985 | Altomare et al. |
| 4,781,936 A | 11/1988 | Nafisi-Movaghar |
| 4,895,938 A | 1/1990 | Teraoka et al. |
| 5,064,675 A | 11/1991 | Jensen et al. |
| 5,275,834 A | 1/1994 | Thibault et al. |
| 5,416,206 A * | 5/1995 | Nagura et al. ................. 536/123 |
| 5,792,461 A | 8/1998 | Bok et al. |
| 5,820,915 A | 10/1998 | Harris |

(Continued)

FOREIGN PATENT DOCUMENTS

EP    0514890 A2    11/1992

(Continued)

OTHER PUBLICATIONS

International Search Report of PCT/EP2010/059766 mailed Oct. 20, 2010.

(Continued)

*Primary Examiner* — David A Reifsnyder
(74) *Attorney, Agent, or Firm* — Sutherland Asbill & Brennan LLP

(57) ABSTRACT

A process for dewatering biomass material comprising polysaccharide and water. The process comprises wetting the biomass material with a wetting composition comprising an alcohol to form a biomass slurry comprising wetted biomass material and a liquid component, mechanically separating a portion of the liquid component from the biomass slurry, and mechanically separating at least a portion of the water from the wetted biomass material. A process for extracting polysaccharide from the biomass material and a dewatered biomass material are also disclosed.

24 Claims, 4 Drawing Sheets

U.S. PATENT DOCUMENTS

| | | | |
|---|---|---|---|
| 5,863,593 A | 1/1999 | Juarez | |
| 5,962,044 A | 10/1999 | Harris | |
| 5,962,756 A | 10/1999 | Koch et al. | |
| 6,183,806 B1 | 2/2001 | Ficca et al. | |
| 6,482,942 B1 | 11/2002 | Vittori | |
| 6,528,099 B1 | 3/2003 | Garti et al. | |
| 6,787,177 B1 * | 9/2004 | Crandall et al. | 426/615 |
| 7,138,152 B2 | 11/2006 | Allen et al. | |
| 7,166,315 B2 | 1/2007 | Hartal et al. | |
| 7,235,275 B2 | 6/2007 | Kotach et al. | |
| 7,527,820 B2 | 5/2009 | Allen et al. | |
| 2003/0166608 A1 | 9/2003 | Pongsamart | |
| 2004/0131748 A1 | 7/2004 | Allen et al. | |
| 2005/0113730 A1 | 5/2005 | Runeman et al. | |
| 2009/0176286 A1 * | 7/2009 | O'Connor et al. | 536/128 |

FOREIGN PATENT DOCUMENTS

| | | |
|---|---|---|
| EP | 0761692 A2 | 12/1997 |
| FR | 2832027 A1 | 5/2003 |
| GB | 453877 A | 9/1936 |
| GB | 1332985 A | 10/1973 |
| WO | 9948382 A1 | 9/1999 |
| WO | 0138400 A2 | 5/2001 |
| WO | 03003818 A2 | 1/2003 |
| WO | 2007120210 A2 | 10/2007 |

OTHER PUBLICATIONS

Written Opinion of the International Searching Authority of PCT/EP2010/059766 mailed Oct. 20, 2010.

International Search Report of PCT/EP/2011/073934 mailed Apr. 17, 2012.

Written Opinion of the International Searching Authority of PCT/EP/2011/073934 mailed Apr. 17, 2012.

* cited by examiner

DEWATERING BIOMASS MATERIAL COMPRISING POLYSACCHARIDE, METHOD FOR EXTRACTING POLYSACCHARIDE FROM BIOMASS MATERIAL, AND DEWATERED BIOMASS MATERIAL

FIELD OF INVENTION

This invention relates to polysaccharide materials and more particularly relates to dewatering of polysaccharide containing materials.

BACKGROUND OF INVENTION

Polysaccharides such as pectin and carrageenan are useful as colloidals in many applications including, but not limited to food preparation. Polysaccharides can be extracted from biomass materials containing polysaccharides and such biomass materials may include citrus fruit peel, apple pomace, sugar beet residue from sugar production, sunflower residue from oil extraction, potato residue from starch extraction from potatoes, red seaweed and brown seaweed.

Some biomass materials contain juice, essential oil, sugar, water, or combinations thereof. Often, materials such as juice, essential oils, and sugar are removed or extracted from the biomass material and the pectin is then extracted from the remaining biomass material. Such biomass material may contain substantial amounts of water including water naturally present in the material and water added to the material during extraction of sugar or other components.

In countries that do not have adequate domestic sources of polysaccharide containing biomass material, biomass material from other countries may be imported and are often transported over long distances for polysaccharide extraction. Thus, it may be necessary for economic reasons to remove substantial amounts of water from the polysaccharide containing biomass material before transport of the biomass material over long distances. Polysaccharide containing biomass materials are typically dried for transportation by direct heating with combusted natural gas. Use of large quantities of water to extract non-polysaccharide containing biomass material components such as sugar from biomass material and cleaning the effluent water from this process may be economically and environmentally undesirable. Furthermore, drying wet polysaccharide containing biomass material by direct heating with combusted natural gas may also be economically and environmentally undesirable. Consequently, there may be a need for a method for treating and dewatering polysaccharide containing biomass material which uses less water, and therefore produces less effluent, or which reduces energy consumption and emission of greenhouse gases such as $CO_2$, or both.

SUMMARY OF INVENTION

This invention addresses one or more of the above-described needs by providing a process for dewatering biomass material comprising polysaccharide and water, in which the process comprises wetting the biomass material with a wetting composition comprising an alcohol to form a biomass slurry comprising wetted biomass material and a liquid component, mechanically separating at least a portion of the liquid component from the biomass slurry, and mechanically separating at least a portion of the water from the wetted biomass material. Without wishing to be bound by theory, the alcohol in the wetting composition appears to facilitate mechanical separation of water from the wetted biomass material.

According to another aspect of the present invention, a process for extracting polysaccharide from a biomass material comprising the polysaccharide in water is provided. This process comprises wetting the biomass material with a wetting composition comprising an alcohol to form a biomass slurry comprising wetted biomass material and a liquid component, mechanically separating at least a portion of the liquid component from the biomass slurry, mechanically separating at least a portion of the water from the wetted biomass material to form dewatered biomass material, and extracting at least a portion of the polysaccharide from the dewatered biomass material.

According to still another aspect of this invention, an alcohol washed and pressed polysaccharide containing biomass material is provided. This biomass material comprises dry matter in an amount from about 35 to 60% by weight of the biomass material and residual sugar in an amount from about 3 to 30% by weight of the biomass material.

Embodiments of this invention are set forth below in the following detailed description, drawings, and claims.

DETAILED DESCRIPTION OF EMBODIMENTS

Figure 1:
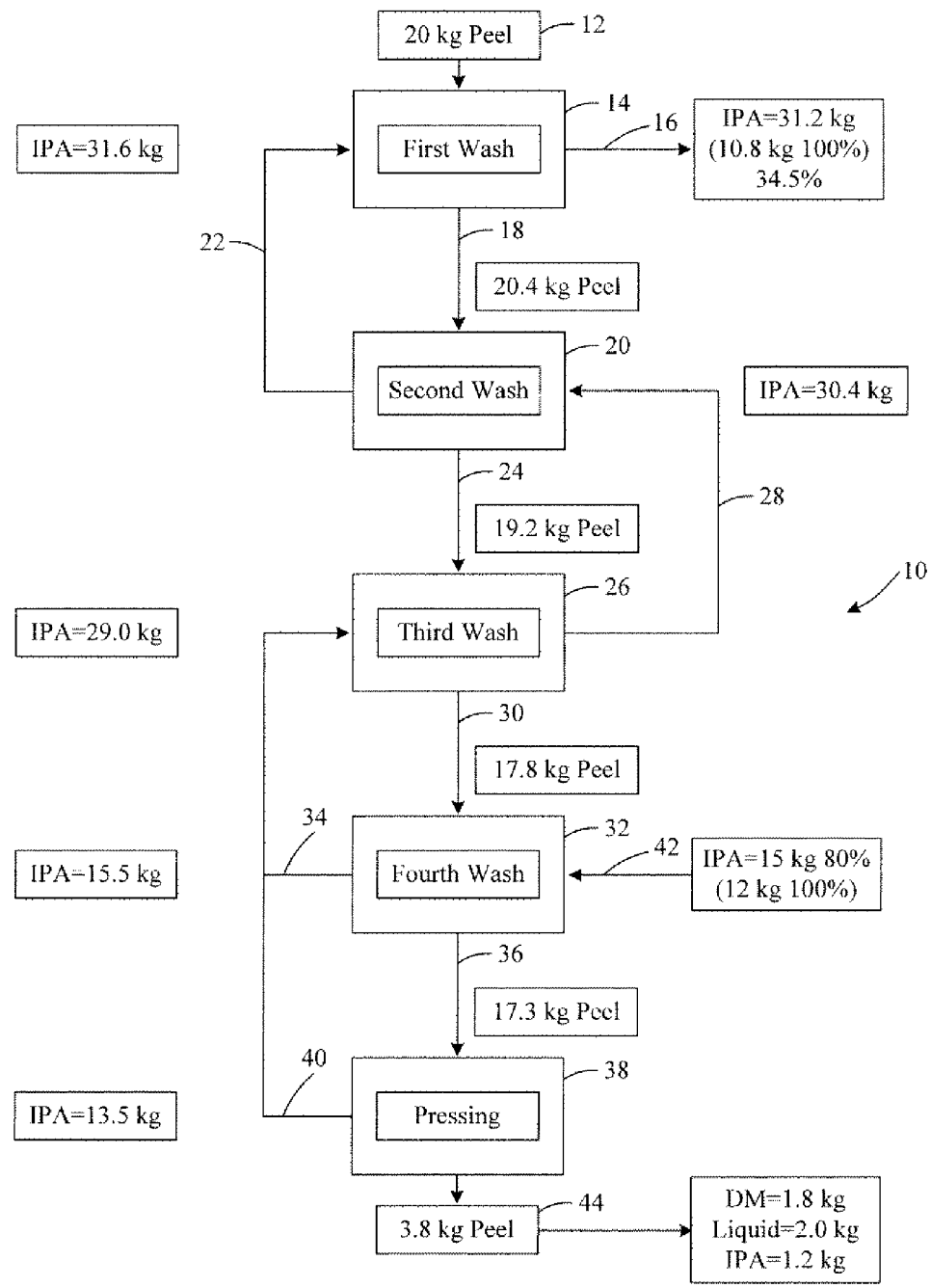
FIG. 1 is a schematic diagram of a four step countercurrent ethanol alcohol wash with a single pressing in accordance with an embodiment of this invention.

As summarized herein above, this invention encompasses a method for dewatering biomass material comprising polysaccharide, a method for extracting polysaccharide from biomass material, and a dewatered biomass material comprising polysaccharide.

According to embodiments of this invention, biomass materials comprising a polysaccharide and water are dewatered for subsequent extraction of at least a portion of the polysaccharide in the biomass material. Suitable polysaccharide containing biomass materials include, but are not limited to citrus fruit peel, apple pomace, from sugar beet residue from sugar extraction, sunflower residue from oil extraction, potato residue from starch production, and other pectin containing biomass material. In addition, other suitable polysaccharide containing biomass materials for embodiments of this invention include, but are not limited to red seaweed containing carrageenan and agar, and brown seaweed containing alginate.

According to certain embodiments of the present invention, suitable polysaccharide containing biomass material includes citrus fruit peel, such as, but not limited to orange peel, lemon peel, lime peel, and grapefruit peel. Dry citrus peel is an important raw material in the manufacture of pectin, but the cost of drying citrus peel is high and may amount to about half of the cost of making dry citrus peel. Citrus peel has been conventionally dried with direct heating from combusting natural gas.

Before dewatering in accordance with embodiments of this invention, the polysaccharide containing biomass material may be subject to an extraction process to extract one or more other components of the biomass material, such as juice and essential oils from citrus fruit, sugar from sugar beets, sunflower oils from sunflower seeds, apple juice from apple fruit, and starch from potatoes. Furthermore, citrus peel may be subjected to aqueous washing for removal of sugar from the peel.

Not wishing to be bound by theory, it is believed that polysaccharides present in biomass material may bind water, thereby making removal of water from polysaccharide containing biomass material by pressing difficult. Surprisingly, treating polysaccharide containing biomass material with alcohol in accordance with embodiments of this invention causes the polysaccharide in situ to loose its water binding ability and thereby makes pressing possible and increases the dry matter in the proportion of the polysaccharide containing biomass material. As used herein, dry matter refers to material in the biomass material that remains after such material is dried at 65° C. to 70° C. for 20 to 24 hours.

Prior to dewatering, the polysaccharide containing biomass material may be comminuted by chopping, cutting, grinding, or other means. According to certain embodiments, the polysaccharide containing biomass material may be cut to an average particle size in the range from about 10 mm to about 30 mm, the particle size being determined by measuring the largest dimension of the particle.

According to certain embodiments of the present invention, the biomass material comprising polysaccharide and water is wetted with a wetting composition comprising an alcohol to form a biomass slurry comprising wetted biomass material and a liquid component. According to certain embodiments, the wetting composition is added to the biomass material in an amount sufficient to cover the biomass material. According to certain embodiments, the step of wetting the biomass material comprises washing the biomass material with the wetting composition and may include agitating the biomass slurry. The biomass material may be washed once with the wetting composition or may be washed a plurality of times with the wetting composition. According to certain embodiments, the biomass material is washed with the wetting composition 2 to 4 times. After each alcohol wash, the process includes mechanically separating at least a portion of the liquid component from the biomass slurry and, according to certain embodiments, comprises draining the liquid component from the biomass material such as with a bow sieve or other separation device.

The wetting composition comprises alcohol and suitable alcohols include but are not limited to ethanol, isopropanol, and combinations thereof. According to certain embodiments, alcohol is present in the wetting composition in an amount from about 40 to about 85% by weight of the wetting composition or at least about 70% by weight of the wetting composition. According to certain embodiments, the wetting composition may also include water in addition to alcohol, and in some embodiments, water constitutes all or substantially the remainder of the wetting composition in addition to the alcohol.

According to certain embodiments, the pH of the liquid component of the biomass slurry may range from about 4 to about 7, the temperature of the liquid component of the biomass slurry may range from about 20° C. to about 50° C. or from about 20° C. to about 30° C. and the duration of each washing step may range from about 10 minutes to about 30 minutes or from about 15 minutes to about 20 minutes.

According to certain embodiments, the dewatering process further comprises mechanically separating at least a portion of the water from the wetted biomass material. Furthermore, according to certain embodiments, the dewatering process further comprises mechanically separating at least a portion of the water and at least a portion of the alcohol from the wetted biomass material. In embodiments in which the wetting composition comprises alcohol and water, the alcohol may be separated from the wetted biomass material together as an azeotrope. According to certain embodiments, this may be done by pressing the wetted biomass material. According to particular embodiments, the pressure during pressing may range from about 0.5 bar to about 8 bar or from about 2 bar to about 4 bar and the duration of pressing may range from about 1 minute to about 25 minutes, or about 10 minutes to about 25 minutes, or about 15 minutes to about 25 minutes. According to a certain embodiment, the pressing step may be carried out with a screw press.

According to a particular embodiment, the polysaccharide containing biomass material may be subjected to a single alcohol wash with the wetting composition followed by a single pressing. When using ethanol in this embodiment, the concentration of ethanol in the wetting composition may be at least 60% by weight of the wetting composition, whereas when using isopropanol, the concentration of the isopropanol in the wetting composition may be at least about 40% by weight of the wetting composition. However, in embodiments using more dense biomass material such as sugar beet material after sugar extraction or potato pulp from starch production, higher alcohol concentrations and longer alcohol washing time may be used. In such embodiments, the alcohol concentration may range from about 60% to about 80% by weight of the wetting composition or from about 70% to about 80% by weight of the wetting composition, the washing duration may range from about 30 minutes to 24 hours, or 30 minutes to about 6 hours, or about 1 hour to about 3 hours. According to a certain embodiment, a marginally higher dry matter content in the biomass material may be achieve by pressing the washed and pressed biomass material a second time.

According to certain embodiments, the wetting step in the dewatering process may comprise washing the biomass material with the wetting composition a plurality of washings and the step of mechanically separating at least a portion of the liquid component from the biomass slurry may comprise mechanically separating at least a portion of the liquid component from the biomass slurry after each of the plurality of washings.

According to particular embodiments, the plurality of washings may number of about 2 to about 4 consecutive steps of washing the biomass material with alcohol and pressing after each wash. In this embodiment, the alcohol used may have the strength of about at least 70% by weight of the wetting composition to avoid loss of pectin, the alcohol in the wetting composition may comprise isopropanol or ethanol or both, the duration of each washing step may range from about 20 to about 30 minutes for a low amount of residual sugar in the biomass material, the pH of the liquid component of the biomass slurry may range from about 4 to about 7, and the temperature of the liquid component of the biomass slurry may range from about 20° C. to about 50° C. or from about 20° C. to about 30° C. According to this embodiment, pressing may be performed once or several times. When using only two washings, two or three pressings increase the amount of dry matter in the biomass material and reduce the residual sugar content in the biomass material, but with more washing steps, one pressing step may be adequate. According to this embodiment, the duration of pressing the biomass material may range from about 1 minute to about 25 minutes or 15 minutes to about 25 minutes and the pressure applied may range from about 0.5 bar to about 8 bar or from about 2 bar to about 4 bar.

According to a certain embodiment, the plurality of washings may be conducted countercurrently followed by a single pressing step at the end. According to this embodiment, the number of countercurrent washings may range from about 2 to about 4, the alcohol concentration in the first of the washings may range from about 40% to about 50% by weight of the wetting composition or about 45% to about 50% by weight of the wetting composition as measured on gas chromatography, the alcohol concentration in the wetting composition in the last washing may be about 80% by weight of the wetting composition. According to this embodiment, suitable alcohols may be isopropanol or ethanol or a combination of both, the duration of each washing step may range from about 10 minutes to about 30 minutes or from about 15 minutes to about 20 minutes, the pH of the liquid component of the biomass slurry may range from about 4 to about 7, and the temperature of the liquid component of the biomass slurry may range from about 20° C. to about 50° C. or from about 20° C. to about 30° C. According to this embodiment, the pressing step may be carried out on any industrial pressing device and the duration of the pressing step may range from about 1 minute to about 25 minutes or from about 10 minutes to about 25 minutes. According to a certain embodiment, the pressing device may be single screw press-type using a counter pressure in the range from about 0.5 bar to about 4 bar or from about 2 bar to about 4 bar.

According to certain embodiments, the step of mechanically separating at least a portion of the water from the wetted biomass material is carried out such that the dewatered biomass material comprises dry matter in an amount from about 35% to about 60% by weight of the dewatered biomass material or from about 45% to about 60% by weight of the dewatered biomass material. In addition, according to certain embodiments, the residual sugar in the dewatered biomass material ranges from about 3% to about 30%, or from about 3% to about 20%, or from about 3% to about 15% by weight of the dewatered biomass material.

When the dry matter is present in the dewatered biomass material in an amount of at least about 45%, or from about 45% to about 60%, or from about 45% to about 55% by weight of the dewatered biomass material, the dewatered biomass material is combustible without further drying. According to certain embodiments of this invention, the process for dewatering biomass material may further comprise combusting at least a portion of the dewatered biomass material to form heat and this heat may be used in the dewatering process, such as to heat the wetting composition or in certain embodiments, dry the dewatered biomass material, or in other heating applications. According to certain embodiments, such a heating system may be supplemented by combusting other biomass materials such as sugar cane waste or wood. Thus, according to a certain embodiment of this invention, the dewatering process may further comprise drying the biomass material with heat after the step of mechanically separating at least a portion of the water from the wetted biomass material to form dried dewatered biomass material. Likewise, this dried dewatered biomass material may be combusted to form heat and the heat may be used in the dewatering process. Drying the dewatered biomass material may reduce the cost of transporting the dewatered biomass material over long distances. According to another embodiment, heat produced from dewatered biomass may be used in applications other than the biomass dewatering process to further decrease the need for other heat or energy producing resources such as oil, natural gas, and the like.

According to embodiments of this invention, the dewatered biomass material may be used in the production of polysaccharides. According to a particular embodiment, a process for extracting polysaccharides from a biomass material comprising polysaccharide and water comprises wetting the biomass material with a wetting composition comprising an alcohol to form a biomass slurry comprising wetted biomass material and a liquid component, mechanically separating at least a portion of the liquid component from the biomass slurry, mechanically separating at least a portion of the water from the wetted biomass material to form dewatered biomass material, and extracting at least a portion of the polysaccharide from the dewatered biomass material. In accordance with a certain embodiment, the steps of wetting and mechanically separating are conducted at a first location, the polysaccharide extracting step is conducted at a second location removed from the first location, and the process further comprises transporting at least a portion of the dried dewatered biomass material from the first location to the second location. The resulting dewatered biomass material may be transported over long distances at more economical prices than biomass material dewatered by conventional means.

In accordance with another embodiment, the polysaccharide extraction process may further comprise drying the biomass material with heat after the step of mechanically separating at least a portion of the water from the biomass material to form dried dewatered biomass material. This may further reduce the cost of transporting the dried dewatered biomass material.

Furthermore, the polysaccharide resulting from extraction in accordance with such embodiments of this invention may be characterized by the identical or similar quality as polysaccharides obtained from the same starting materials, but without having undergone the process described by such embodiments of the present invention.

In addition, there are several effective uses of alcohol washed and pressed polysaccharide containing biomass material in accordance with embodiments of this invention. Such embodiments include the use of alcohol washed and pressed polysaccharide containing biomass material in food and non-food products. As used herein, food products include solid, liquid, semi-solid, gelatinous, and flowable foods, and encompasses beverages. Embodiments of this invention include a method for preparing a food comprising adding alcohol washed and pressed polysaccharide containing biomass material to a food base material. Suitable food base materials include any edible materials including but not limited to water, dairy products, confections, fruit juices, vegetable juices, sauces, syrups, bakery products, and the like.

The lower cost of dewatering biomass material in accordance with the embodiments of this invention may make use of the dewatered biomass material more economical for certain lower cost application such as alkalinity controlling applications. One such application encompasses the use of alcohol washed and pressed polysaccharide containing biomass material in animal farms to neutralize ammonia and another is the use of alcohol washed and pressed polysaccharide containing biomass material to control the skin pH of animals or humans. Such an application in poultry farms may reduce or eliminate hock burns. Thus, one embodiment of this invention is a method for controlling the pH of animal or human skin comprising exposing to the skin a composition comprising an alcohol washed and pressed polysaccharide containing biomass material. Another embodiment is a method for controlling airborne ammonia at animal farms comprising exposing animal waste discharged by animals at the animal farm to a composition comprising the alcohol washed and pressed polysaccharide containing biomass material.

According to embodiments of this invention, the alcohol washed and pressed polysaccharide containing biomass material may be used in wet form or dry form in applications described above. According to certain embodiments, the alcohol washed and pressed polysaccharide containing biomass material may be ground, and in particular embodiments may be ground to flour like consistency.

Figure 2:
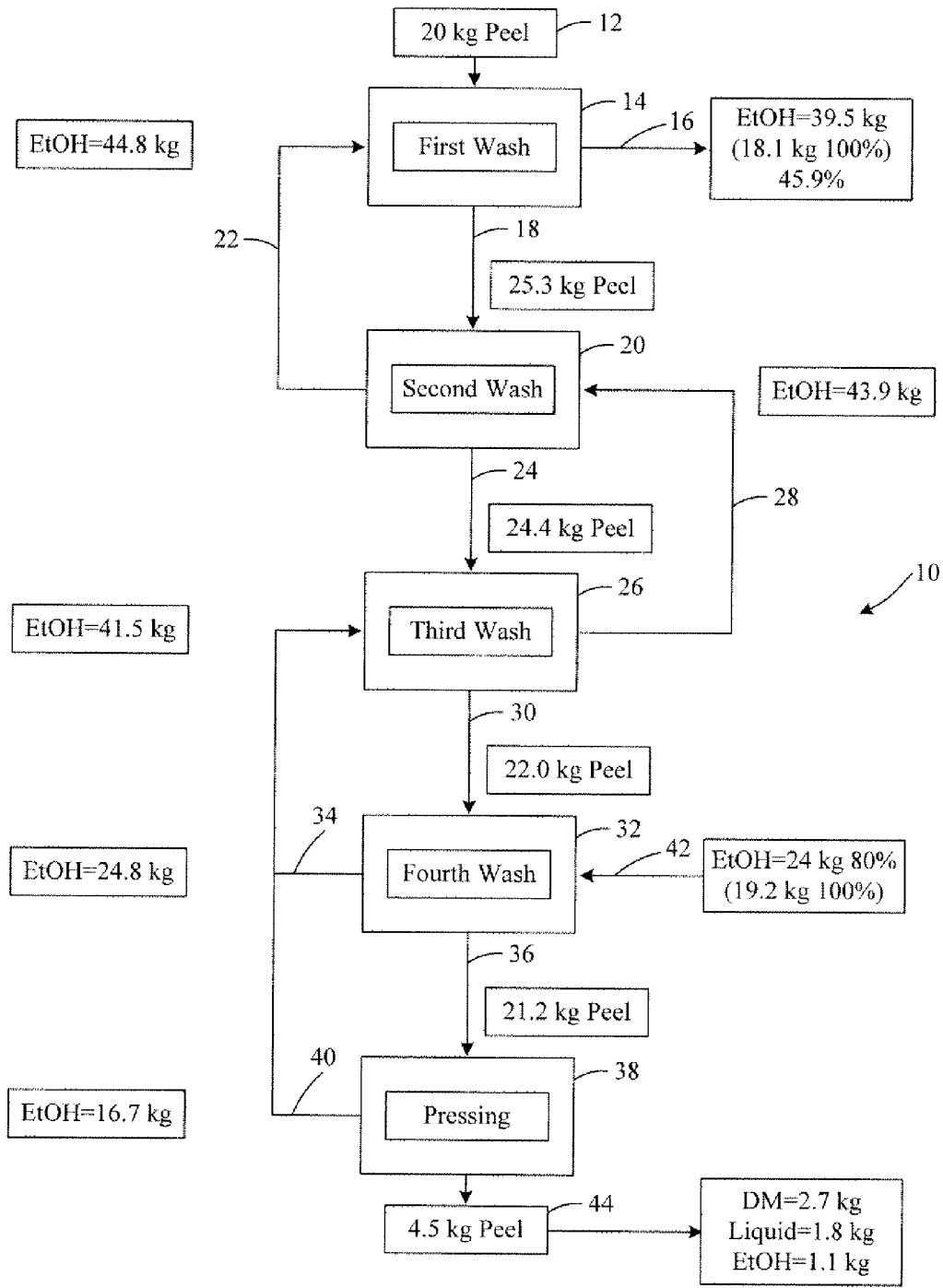
FIG. 2 is a schematic diagram of a four-step countercurrent isopropyl alcohol wash with a single pressing step.

Turning to FIGS. 1 and 2, four step countercurrent alcohol wash dewatering processes are illustrated in accordance with certain embodiments of this invention. The processes illustrated in FIGS. 1 and 2 are identical except that different alcohols are used. Isopropanol is used in the process illustrated in FIG. 1 and ethanol is used in the process illustrated in FIG. 2. Accordingly, the reference numerals are the same for both figures and the process is described only once hereinbelow in regard to these FIGS. 1 and 2. Both of these figures also illustrate a mass balance which is described further hereinbelow in the description of the examples of certain embodiments of the invention.

FIGS. 1 and 2 both illustrate a dewatering process schematic 10 which begins with citrus peel 12 being added to a first wash 14 comprising alcohol. Effluent 16 from the first wash 14 is discharged from the system and orange peel from the first wash 18 is delivered to the second wash 20 which also comprises alcohol. Effluent 22 from the second wash is fed back to the first wash 14 in countercurrent fashion. The orange peel from the second wash 24 is fed to the third wash 26 which comprises alcohol and effluent 28 from the third wash 26 is fed countercurrently to the second wash 20. Orange peel 30 from the second wash 26 is fed to the fourth wash 32 which comprises alcohol. Effluent 34 from the fourth wash 32 is fed to the third wash 26. Orange peel 36 from the fourth wash 32 is fed to a pressing station 38 and the effluent 40 from the pressing station 38 is fed countercurrently to the third wash 26 as well. Alcohol 42 is added to the system via the fourth wash 32. The pressing station 38 discharges dewatered orange peel 44.

EXAMPLES

The present invention is further illustrated by the following examples, which are not to be construed in any way as imparting limitations upon the scope thereof. On the contrary, it is to be clearly understood that resort may be had to various other embodiments, modifications, and equivalents thereof which, after reading the description therein, may suggest themselves to those skilled in the art without departing from the scope of the appended claims. Unless otherwise specified, %'s are by weight.

Test Procedures

Test procedures used to evaluate samples from embodiments of this invention in accordance with the Examples were as follows:

Determination of Degree of Esterification (DE) and Galacturonic Acid (GA) in Non-Amide Pectin Apparatus:
1. Analytical balance
2. Glass beaker, 250 ml, 5 pieces
3. Measuring glass, 100 ml
4. Vacuum pump
5 Suction Flask
6. Glass filter Crucible no. 1 (Büchner funnel and filter paper)
7. Stop watch
8. Test tube
9. Drying cabinet at 105° C.
10. Desiccator
11. Magnetic stirrer and magnets
12. Burette (10 ml, accuracy ±0.05 ml)
13. Pipettes (20 ml: 2 pieces, 10 ml: 1 piece)
14. pH-meter/auto burette or phenolphthalein Chemicals:
1. Carbon dioxide-free water (deionized water)
2. Isopropanol (IPA), 60% and 100%
3. Hydrochloride (HCl), 0.5 N and fuming 37%
4. Sodium hydroxide (NaOH), 0.1 N (corrected to four decimals, e.g. 0.1002), 0.5 N
5. Silver nitrate ($AgNO_3$), 0.1 N
6. Nitric acid ($HNO_3$), 3 N
7. Indicator, phenolphthalein, 0.1%

Procedure—Determination of % DE and % GA
(Acid alcohol: 100 ml 60% IPA+5 ml HCl fuming 37%):
1. Weigh 2.0000 g pectin in a 250 ml glass beaker.
2. Add 100 ml acid alcohol and stir on a magnetic stirrer for 10 min.
3. Filtrate through a dried, weighed glass filter crucible.
4. Rinse the beaker completely with 6×15 ml acid alcohol.
5. Wash with 60% IPA until the filtrate is chloride-free* (approximately 500 ml).
6. Wash with 20 ml 100% IPA.
7. Dry the sample for 2½ hours at 105° C.
8. Weigh the crucible after drying and cooling in desiccator.
9. Weigh accurately 0.4000 g of the sample in a 250 ml glass beaker.
10. Weigh two samples for double determination. Deviation between double determinations must max. be 1.5% absolute. If deviation exceeds 1.5% the test must be repeated.
11. Wet the pectin with approx. 2 ml 100% IPA and add approx. 100 ml carbon dioxide-free, deionized water while stirring on a magnetic stirrer.

*(Chloride test: Transfer approximately 10 ml filtrate to a test tube, add approximately 3 ml 3 N $HNO_3$, and add a few drops of $AgNO_3$. The filtrate will be chloride-free if the solution is clear, otherwise there will be a precipitation of silver chloride.)

The sample is now ready for titration, either by means of an indicator or by using a pH-meter/auto burette.

Procedure—Determination of % DE Only
(Acid alcohol: 100 ml 60% IPA+5 ml HCl fuming 37%):
1. Weigh 2.00 g pectin in a 250 ml glass beaker.
2. Add 100 ml acid alcohol and stir on a magnetic stirrer for 10 min.
3. Filtrate through a Büchner funnel with filter paper.
4. Rinse the beaker with 90 ml acid alcohol.
5. Wash with 1000 ml 60% IPA.
6. Wash with approximately 30 ml 100% IPA.
7. Dry the sample for approximately 15 min. on Büchner funnel with vacuum suction.
8. Weigh approximately 0.40 g of the sample in a 250 ml glass beaker.
9. Weigh two samples for double determination. Deviation between double determinations must max. be 1.5% absolute. If deviation exceeds 1.5% the test must be repeated.

10. Wet the pectin with approximately 2 ml 100% IPA and add approx. 100 ml deionized water while stirring on a magnetic stirrer.

The sample is now ready for titration, either by means of an indicator or by using a pH-meter/auto burette.

Note: It is very important that samples with % DE<10% are titrated very slowly, as the sample will only dissolve slowly during titration.

Titration using indicator:
1. Add 5 drops of phenolphthalein indicator and titrate with 0.1 N NaOH until change of color (record it as V1 titer).
2. Add 20.00 ml 0.5 N NaOH while stirring. Let stand for exactly 15 min. When standing, the sample must be covered with foil.
3. Add 20.00 ml 0.5 N HCl while stirring and stir until the color disappears.
4. Add 3 drops of phenolphthalein and titrate with 0.1 N NaOH until change of color (record it as V2 titer).

Blind test (Double determination is carried out):
Add 5 drops phenolphthalein to 100 ml carbon dioxide-free or dionized water (same type as used for the sample), and titrate in a 250 ml glass beaker with 0.1 N NaOH until change of color (1-2 drops).

Add 20.00 ml 0.5 N NaOH and let the sample stand untouched for exactly 15 minutes. When standing the sample must be covered with foil.

Add 20.00 ml 0.5 N HCl and 3 drops phenolphthalein, and titrate until change of color with 0.1 N NaOH (record it as B1). Maximum amount allowed for titration is 1 ml 0.1 N NaOH. If titrating with more than 1 ml, 0.5 N HCl must be diluted with a small amount of deionized water. If the sample has shown change of color on addition of 0.5 N HCl, 0.5 N NaOH must be diluted with a small amount of carbon dioxide-free water. Maximum allowed dilution with water is such that the solutions are between 0.52 and 0.48 N.

Titration using pH-meter/Auto burette:
Using Auto burette type ABU 80 the following settings may be applied:

| Sample with | % DE < 10 | Blind test |
|---|---|---|
| Proportional band | 0.5 | 5 |
| Delay sec. | 50 | 5 |
| Speed - V1 | 10 | 5 |
| Speed - V2 | 15 | 5 |

1. Titrate with 0.1 N NaOH to pH 8.5 (record the result as V1 titer).
2. Add 20.00 ml 0.5 N NaOH while stirring, and let the sample stand without stirring for exactly 15 minutes. When standing the sample must be covered with foil.
3. Add 20.00 ml 0.5 N HCl while stirring and stir until pH is constant.
4. Subsequently, titrate with 0.1 N NaOH to pH 8.5 (record the result as V2 titer).

Blind test (Double determination is carried out):
1. Titrate 100 ml carbon dioxide-free or deionized (same type as used for the sample) water to pH 8.5 with 0.1 N NaOH (1-2 drops).
2. Add 20.00 ml 0.5 N NaOH while stirring and let the blind test sample stand without stirring for exactly 15 min. When standing the sample must be covered with foil.
3. Add 20.00 ml 0.5 N HCl while stirring, and stir until pH is constant.
4. Titrate to pH 8.5 with 0.1 N NaOH (record it as B1). Maximum amount allowed for titration is 1 ml 0.1 N NaOH. If titrating with more than 1 ml, 0.5 N HCl must be diluted with a small amount of deionized water. If pH does not fall to below 8.5 on addition of 0.5 N HCl, 0.5 N NaOH must be diluted with a small amount of carbon dioxide-free water. Maximum allowed dilution with water is such that the dilutions are between 0.52 and 0.48 N.

Calculation:

$$V_t = V_1 + (V_2 - B_1)$$

$$\% \text{ DE (Degree of Esterification)} = \{(V_2 - B_1) \times 100\}/V_t$$

$$\% \text{ DFA (Degree of Free Acid)} = 100 - \% \text{ DE}$$

$$\% \text{ GA* (Degree of Galacturonic acid)} = (194.1 \times V_t \times N \times 100)/400$$

*On ash- and moisture-free basis
194.1: Molecular weight for GA
N: Corrected normality for 0.1 N NaOH used for titration (e.g. 0.1002 N)
400: weight in mg of washed and dried sample for titration
% Pure pectin={(acid washed, dried amount of pectin)×100}/(weighed amount of pectin)

Determination of Residual Sugar in Peels
Apparatus
1. Glass beaker, 400 ml
2. Balance (accuracy 0.2 g)
3. Magnet stirrer
4. Magnet
5. Paper filters (coarse) e.g. type AGF 614
6. Drying cabinet at 65-70° C.
7. Büchner funnel
8. Vacuum pump Solutions
1. Isopropanol 50%

Procedure
1. Weigh out about 3 g dry peel in a glass beaker.
2. Add 100 ml 50% isopropanol.
3. Stir for 4 hours on magnet stirrer and filter.
4. Wash the filtrate with 250 ml 50% isopropanol.
5. Place filter and filtrate in drying cabinet at 65-70° C. overnight and determine weight of filtrate.

Calculate the residual sugar in peels:

(Weight of dry peel−weight of dry, washed peel)×100/weight of dry peel

Determination of Molecular Weight, Intrinsic Viscosity and Molecular Weight Distribution in Pectin Based on Orange, Lime and Lemon.

The molecules are separated according to their size by gel permeation chromatography Size Exclusion Chromatography. The effluent from the chromatography column passes three detectors, Refractive Index (RI), Right Angle Laser Light Scattering (RALLS) and a viscosity detector (DP). The Viscotek software converts the detector signals to molecular weight and intrinsic viscosity and calculates weighted averages for the entire population.

Principle
The analyses are performed using SEC (Size Exclusion Chromatography). The principle of SEC is that the molecules are separated on basis of size, the larger molecules eludes first, then the smaller molecules, then salts.

Equipment Analysis and Conditions.
Viscotek Tri-Sec instrument
Viscotek pump VE 1121GPC pump Degasser
Auto sampler AS3500 with Sample prep. module, Thermo Separation Products
Column oven for 3 columns, STH 585 (40° C.)
3 TSK Columns GMPWXL, from Supelco and a guard column.
RALLS detector, Right Angle Laser Light Scattering Detector LD 600
Dual Detector, RI Detector, Refractive Index and Viscometer Detector, Module 250
Data manager, acquisition unit
Computer, Tri-Sec software
Solvent: 0.3 M Li-acetate buffer pH 4.8.
Flow: 1.0 ml/min
Pectin conc.: Approximatly 1 mg/ml
Temperature: 40° C.
Injection volume: 100 μl Full loop.
Analysis time for one run is 50 minutes. Samples are tested by making two runs and comparing them. If there is more than 10 percent deviation (% STDV) between the Mw results, two new runs are made.
Manual Sample Preparation:
Samples known to contain non-soluble material must be manually dissolved and filtrated (0.45 μm filter) prior to injection.
1. 40.0 mg sample is weighed out into a 100 ml Blue Cap bottle.
2. A magnet and 100 ml ethanol are added.
3. The sample is placed at a magnetic stirrer including a 75° C. water bath or Block heater.
4. While gently stirring, 40 ml of solvent is added.
5. The bottle cap is closed and the sample is stirred gently at 75° C. for 30 min.
6. The sample is cooled in an approx. 20° C. water bath until room temperature is reached.

Sample Preparation Using Auto Sampler AS3500:
Weigh out approx. 1.5 mg pectin in an auto sampler vial. This is placed in the auto sampler rack. Use template 4 from the AS3500 auto sampler. The following units in the auto sampler are used:
Dilution cycles: 3
Heater: ON Temp: 70° C.
1—Load 20 μl solvent S-1 (S-1=96% ethanol)
5—Add 10 μl to sample
11—Load 1500 μl solvent S-2 (S-2=0.3 M Li-acetate buffer)
15—Add 1300 μl to sample (0.1% pectin solution—1 mg/ml)
16—Mix for 9.9 minute
18—Mix for 9.9 minute
19—wait for 5.0 min.
Enable Overlay: YES (starts the next sample preparation before end of analysis for running sample)
Run time at the auto sampler is set at 50 min or more. 100 ml full loop injection is used. When the auto sampler is used, the sample is automatically filtrated by a 0.5 mm in-line filter placed after the auto sampler loop. As control sample, use a Dextran with the molecular weight 70,000 Daltons, concentration about 3.0 mg/ml and a pectin sample with a known Mw. In addition the RI detector, the recovery, must be controlled with a pectin solution with a known concentration. For daily control use the Dextran standard. For weekly control use the pectin sample. For monthly control of the recovery use the pectin solution. Dextran T 70 Mw 70,000 and Pullulan Mw 212,000 are used for calibration. Calibration is only performed by a Viscotek supervisor.
For registration of instrument-data, maintain a logbook with data about purging, flow, pump pressure, oven temperature, detector signals, bridge balance and recovery.

Eluent preparation 1 L
30,603 g Lithium acetate dihydrate M=102.01
17,157 ml (18.02 g) 100% acetic acid
MilliQ-water up to 1 L
0.25 g Sodiumazid for preservation
Ultra filtration 0.2μ after dissolution
All chemicals must be analytical grade.
Approval Criterion
To test a sample, always make double determination and compare results. If there is more than 10 percent deviation (% STDV) between the Mw results, a new double determination must be made. For pectin standards the approval criterion is 10 percent (% STDV) at the Mw result. For Dextran 70,000 Daltons the approval criterion is 5 percent deviation to the standard molecular weight at the Mw result.
Determination of Calcium Sensitivity
Principle
A fixed amount of pectin is dissolved in hot water and solution pH is adjusted to 3.60 using 3.0M acetate buffer. Subsequent addition of 272 ppm calcium increases the viscosity. The calcium sensitivity, CS-99-2, is defined as the viscosity (in centipoises) for this solution after 19 hours at 5° C.
Apparatus
1. Viscosity glasses, 48 mm internal diameter, height 110 mm
2. Magnetic stirrer
3. Magnetic stir bars, triangular: length 40 mm, side 6 mm
4. Water bath (75° C.) with magnetic stirrer or appropriate stirring block thermostat
5. Foil or other heat tolerant covering material, e.g. watch glasses
6. Volumetric pipettes 5 and 20 ml (or adequate dispensers)
7. Volumetric flasks: 2000 ml (or 5000 ml)
8. pH-meter with combination electrode
9. Laboratory scale
10. Fume hood
11. Brookfield LVT Viscometer without protective loop
Chemicals
Isopropanol (2-propanol), 100%
Calcium chloride dihydrate ($CaCl_2$, $2H_2O$)
Sodium acetate trihydrate ($C_2H_3NaO_2$, 3 $H_2O$)
Acetic acid ($C_2H_4O_2$), >99%
Ion-exchanged water
Reagents
3.0M sodium acetate buffer pH 3.60 (2000 ml)
Dissolve 81.64 g sodium acetate trihydrate in approx. 1200 ml ion exchanged water in a volumetric beaker. Transfer this solution quantitatively to a 2000 ml volumetric measuring flask.
In a fume hood, add 309 ml acetic acid. Mix the contents and add ion-exchanged water to 2000 ml. Solution pH should be 3.60±0.05 and must be verified prior to use.
M sodium acetate buffer pH 3.60 (5000 ml)
Dissolve 204.00 g sodium acetate trihydrate in approx. 1200 ml ion exchanged water in a volumetric beaker. Transfer this solution quantitatively to a 5000 ml volumetric measuring flask.
In a fume hood, add 772 ml acetic acid. Mix the contents and add ion-exchanged water to 5000 ml. Solution pH should be 3.60±0.05 and must be verified prior to use.
Calcium chloride solution
Weigh 32.0 g calcium chloride dihydrate into a weighing dish or volumetric beaker and transfer quantitatively to a 1000 ml volumetric measuring flask. Add approximately 200 ml ion exchanged water, mix the content, and add ion-exchanged water to 1000 ml.

Procedure
1. Weigh pectin into a viscosity glass; for un-standardized pectin: 0.64 g (i.e. 0.4%), and for standardized pectin: 0.80 g (i.e. 0.5%)
2. Add 5.0 ml is isopropanol.
3. Stir the sample at a magnetic stirrer while adding 130 ml boiling (>85° C.) H₂O. It is important that the viscosity glass is covered (with e.g. foil) during all agitation steps, i.e. (3)-(5).
4. Add 20 ml 3.0 M sodium acetate buffer pH 3.60 within 1 min after water addition (3).
5. Within 1 min after (4), place the sample in a water bath at 75° C. with continued magnetic stirring for 10±2 min.
6. If the sample contains visual lumps, the sample must be discarded, and the complete dissolving procedure must be repeated.
7. Stir the sample with vortex of approx. 2 cm. Add swiftly (within 2 sec) 5 ml calcium chloride solution to the sample and mix for approx. 10 sec.

Important

If the vortex disappears while the calcium is added and/or local gelation or entrapped air bubbles are observed, the sample must be marked pre-gelled as a result of the analysis. Notably, leaving the sample with the intention of spontaneous bubble disappearance and proceeding as for "normal" samples, the obtained result will be too low. In such cases, the analysis might be performed using a lower pectin concentration.

1. Remove the magnet in order not to decrease viscosity prior to its measurement and cover the glass with e.g. foil.
2. Within 5 min from (7), place the sample in a 5° C. water bath for 19±3 hours. Make sure that the water level of water bath is equal to the level of the sample surface.
3. If air bubbles are present at the sample surface, gently remove these prior to viscosity measurements using a Brookfield LVT Viscometer without its protective loop. Measure sample viscosity at 5° C. using spindle No. 2 and spindle speed 60 rpm. Take the Viscometer reading after 1 min.
4. If reading is below 10, change to spindle No. 1 and re-measure at 60 rpm after 1 min.
5. If reading is above 100, place the sample in the 5° C. water bath for 19±3 hours and re-measure the 1-min viscosity using spindle No. 3 at 60 rpm.
6. Calculate the viscosity in centipoises by multiplying the Viscometer reading by the appropriate spindle-dependent factor. The CS value is equal to the calculated viscosity.

Determination of is Isopropanol in Wetting Composition

Principle

Samples are analyzed on gas chromatograph. The individual samples are added a solution of tert butanol.

Figure 3:
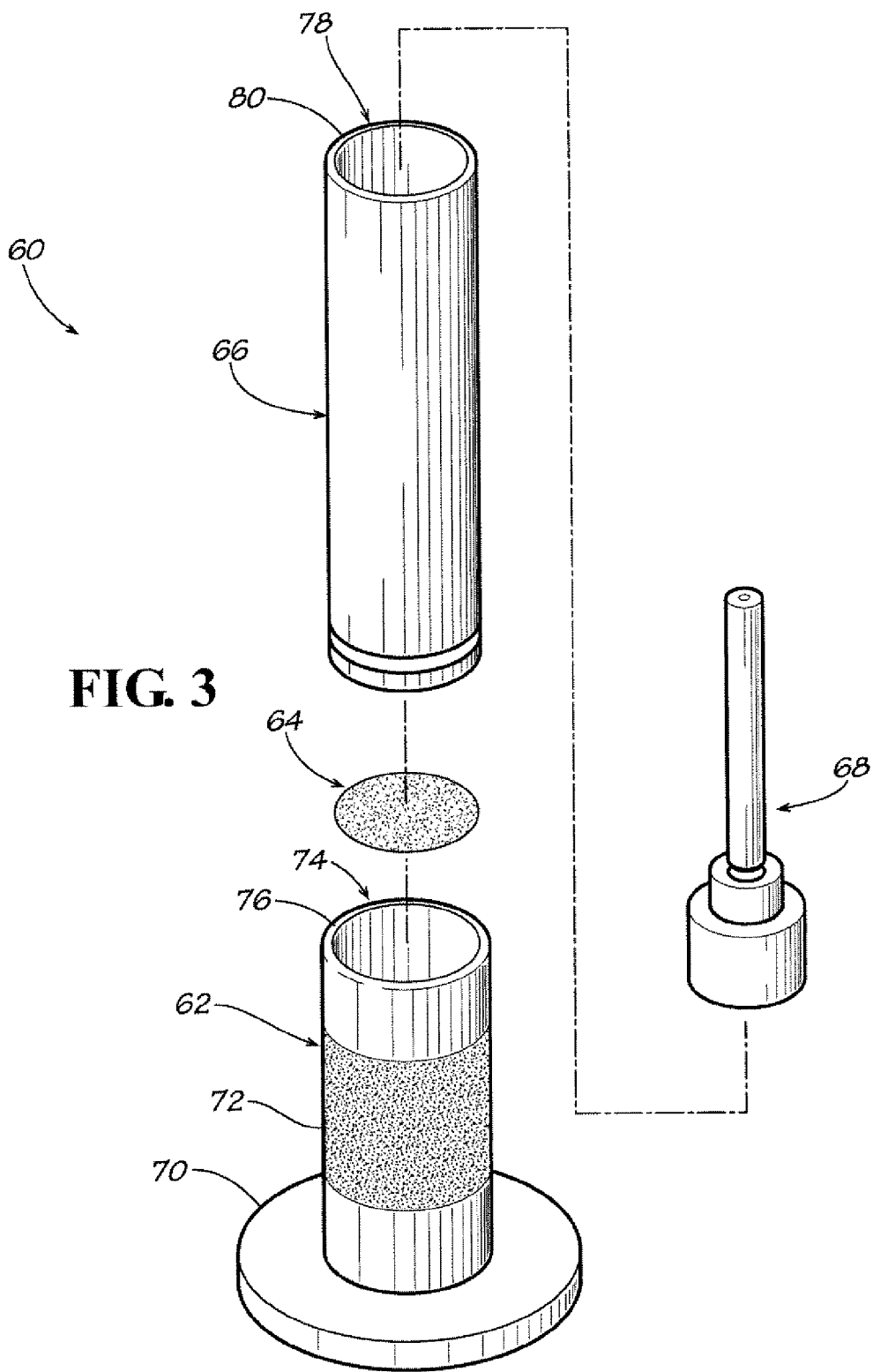
FIG. 3 is an exploded view of a pressing cell for use in pressing fruit peel in accordance with embodiments of this invention.
Figure 4:
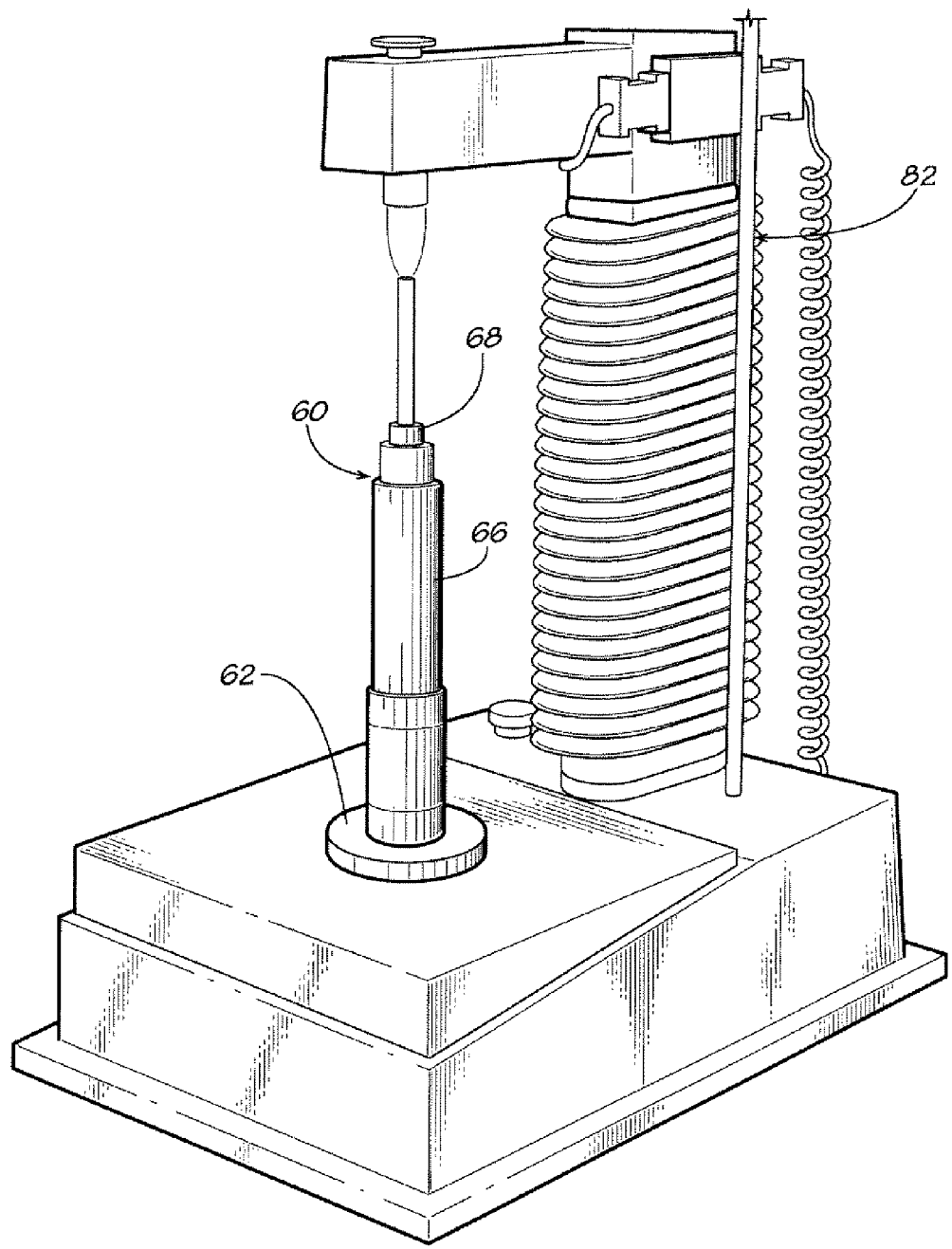
FIG. 4 is a perspective view of the pressing cell in FIG. 3 mounted to an analyzer.

Apparatus
  Analytical balance
  Auto pipette
  Pipettes
  50 and 100 ml measuring flasks Chemicals
  Is propyl alcohol, analytical grade
  Tert butanol, analytical grade
  Deionised water Procedure
1. Weigh about 5.0000 g of wetting composition into a 100 ml measuring flask containing about 20 ml deionised water, and weight the contents with four decimals
2. Fill the flask to the mark with deionised water
3. Transfer 5 ml to a 50 ml measuring flask containing 10 ml 2% (w/v) tert butanol.
4. Fill the flask to the mark with deionised water
5. Transfer samples to vials and inject three times per vial
6. Make up standard samples containing 0.1, 0.2, 0.3 and 0.4% (w/v) isopropanol and 0.4% tert butanol Procedure for Treating Peel in Examples In the following Examples, fruit was processed in laboratory scale experiments, pilot plant scale experiments with consecutive washing and pressing, and pilot plant scale experiments with countercurrent washing and pressing. In addition, pectin was extracted in laboratory scale experiments and pilot plant scale experiments. Those procedures were as described below:

Treatment of Peel in Laboratory Scale
1. Apparatus
2. Potato peeler
3. Glass beakers—1000 ml, 2000 ml
4. Hand held juicer
5. pH-meter
6. TA-XT2 Texture Analyser, Stable Micro Systems
7. Load cells—25 kg, 50 kg.
8. Press cell 60 illustrated in FIGS. 3 and 4. The press cell 60 comprises a pedestal 62, a sieve plate 64 mounted in the pedestal, a cylinder 66 for engaging the pedestal and holding the peel, and a plunger 68 for pressing the peel in the cylinder 66 against the sieve plate 64. The pedestal 62 comprises a base 70 and a hollow cylindrical tube 72 extending upwardly from the base 70 having a first compartment 74 for received liquid removed by pressing the peel. The sieve plate 64 has 1 mm holes through which pressed liquid passes and rests on a shoulder (not shown) within the first compartment 74 of the tube 72 near the top 76 of the tube 72. The peel holding cylinder 66 has a second compartment 78 for receiving the peel and the plunger 68 has a diameter of 28 mm and is reciprocably engaged within the peel holding cylinder 66 through a top opening 80 in the peel holding cylinder. The entire press cell is mounted to a TA-XT2 Texture Analyser 82 (item 6 in this list) for pressing the peel.

Materials
1. Fresh lemon and oranges purchased in the local supermarket
2. Demineralized water
3. 96% ethanol
4. 100% iso propanol
5. 10% nitric acid Procedure
1. The flavedo of the fruit was peel off
2. The fruit was juiced
3. The juiced fruit was cut into small cubes of about 5 mm
4. The cut fruit pieces were washed and pressed
5. The pressed fruit pieces were dried over night at about 68° C.

With a load cell of 25 kg, the pressure used was about 4 Bar and with a load cell of 50 kg, about 8 Bar.

Treatment of Peel in Pilot Plant Scale—Consecutive Washing and Pressing

Equipment:
  100 liter plastic containers
  Pilot plant scale
  Stirrer, IKA Werke RW 44, Germany
  Vincent screw press P-4, USA
  Density measuring device
  25 liter extraction vessel Materials:
Juiced orange peel obtained from Futura, Grontorvet, Denmark
Demineralized water
80% iso propanol
Concentrated nitric acid
Ion exchange resin, Lewatit S-1468, LANXESS, Leverkusen, Germany
Filter aid, diatomaceous earth Washing and Pressing of Peel
1. Upon arrival, the juiced orange peel was submerged and stirred in 80% IPA for 30 minutes
2. The washed peel was pressed on Vincent screw press with a back pressure of 4 bars
3. The pressed peel was covered with 80% IPA and washed in 80% IPA for another 30 minutes
4. The washed peel was pressed on Vincent screw press with a back pressure of 4 bars
5. The washing and pressing cycle was continued until the dry matter of the pressed peel was constant
6. For some runs, the pressed peel was dried and a standard pectin extraction performed:
   18 liters demineralised water
   80 ml nitric acid
   Extraction for 7 hours at 70° C.
   Ion exchange with 50 ml ion exchange resin for 30 minutes while stirring
   Precipitation with three volumes 80% IPA Treatment of Peel in Pilot Plant Scale—Countercurrent
This pilot scale was conducted in accordance with the schematic diagram in FIG. 2.

Equipment:
100 liter plastic containers
Pilot plant juicer, Otto 1800, Centenario, Brazil
Pilot plant scale
Stirrer, IKA Werke RW 44, Germany
Vincent screw press P-4, Vincent Corporation, USA
Cutter, Rex-cutter, 30 liter, Kilia, Germany
Density measuring device
25 liter extraction vessel
Büchner funnel Materials:
Fresh oranges obtained from Futura, Grontorvet, Denmark
Demineralized water
96% ethanol, WWR International ApS, Denmark
Concentrated nitric acid
Ion exchange resin, Lewatit S-1468, LANXESS, Leverkusen, Germany
Filter aid, diatomaceous earth, Celite 545

Washing and Pressing of Peel
7. Fresh oranges were juiced on the juicer
8. About 20 kg peel was cut on the cutter to a particle size of about 10 mm, and was submerged in 80% ethanol about 20 minutes with slight agitation.
9. The peel was drained for alcohol.
10. The drained and cut peel was washed for 20 minutes with ethanol while stirring, either fresh 80% or ethanol from subsequent washing steps and drained on sieve.
11. After five washing steps in countercurrent, the last batch of washed peel was pressed on Vincent screw press with a back pressure of 4 bars
12. For some runs, the pressed peel was dried and a standard pectin extraction performed:
   18 liters demineralized water
   80 ml nitric acid
   Extraction for 7 hours at 70° C.
   Ion exchange with 50 ml ion exchange resin for 30 minutes while stirring
   Precipitation with three volumes 80% IPA Extraction of Pectin in Laboratory Scale
Apparatus
1. Glass beaker—2000 ml
2. Büchner funnel
3. Stirrer with propeller stirrer, Eurostar digital, IKA Werke
4. Nylon cloth Chemicals
1. Demineralized water
2. 62% nitric acid
3. Diatomaceous earth
4. Ion exchange resin, Amberlite SR1L, produced by Rohm&Haas
5. 100% iso propanol
6. 60% iso propanol Procedure
1. About 900 ml demineralised water was heated to 70° C. in a glass beaker equipped with a stirrer and temperature control
2. About 20 g dry peel was added to the water, and the pH is adjusted to 1.7-1.8 by addition of 62% nitric acid.
3. Extraction was carried out at 70° C. for 5 hours while stirring.
4. After extraction, the content of the vessel was filtered on a Büchner funnel using diatomaceous earth as filter aid previously rinsed with a mixture of 10 ml 62% nitric acid and 500 ml demineralised water.
5. The filtered extract was ion exchanged while stirring by adding about 50 ml resin (Amberlite SR1L, produced by Rohm&Haas) per liter of filtered extract. While stirring, the ion exchange was carried out during 20 minutes while stirring.
6. The ion exchanged filtrate was filtered on a Büchner funnel equipped with a cloth.
7. The filtered ion exchanged filtrate was precipitated by adding it to three parts of 100% isopropanol while stirring gently.
8. The precipitate was collected on nylon cloth and pressed by hand to remove as much isopropanol as possible.
9. The hand pressed precipitate was washed once in 60% isopropanol and then dried at about 68° C. in a drying cabinet at atmospheric pressure.
10. After drying, the pectin was milled.

Extraction of Pectin in Pilot Plant Scale
1. 600 g dry peel, 18 liter ion exchanged water and 80 ml 62% nitric acid were mixed in an 18 liter extraction vessel and extracted for 7 hours at 70° C. while stirring.
2. The mixture was filtered on Büchner funnel with diatomaceous earth.
3. The filtrate was ion exchanged with 50 ml ion exchange resin per liter filtrate at 45° C. for 30 minutes.
4. The ion exchange resin was drained on nylon cloth.
5. The ion exchanged filtrate was precipitated in three volumes of 80% iso propyl alcohol.
6. The precipitate was washed once with 60% iso propyl alcohol and dried at 65° C. for 24 hours.

Analysis of Samples from Examples
Examples 1-10 deal with laboratory experiments whereas Examples 11-14 deal with experiments in pilot plant and Examples 15-18 deal with experiments in pilot plan on pectin and carrageenan waste materials.

Example 1

Effects of Alcohol Strength

In the first set of experiments, peel dry matter, pectin yield, residual sugar concentration in the peel DE, and pectin molecular weight $M_w$ were measured after one wash and one pressing under different conditions and the data is shown below in Table 1.

TABLE 1

Dry Matter, Sugar Concentration, Pectin Yield, DE and Molecular Weight of Washed and Pressed Peel.

| Sample No. | Wetting Composition | No. Wash | Wash Time Min | No. Press | Dry Matter Of Pressed peel % | Residual in the Peel Sugar % | Pectin Yield % | DE % | $M_W$ KDalton of Pectin |
|---|---|---|---|---|---|---|---|---|---|
| 9 | 96% EtOH | 1 | 15 | 1 | 20.0 | 25.1 | 17.0 | 74.3 | 240 |
| 10 | 70% EtOH | 1 | 15 | 1 | 17.2 | 21.8 | 17.4 | 72.1 | 218 |
| 11 | 50% EtOH | 1 | 15 | 1 | 14.5 |  | 14.2 | 71.7 | 216 |
| 0 | No wash, no press |  |  |  | 13.0 | 44.7 |  |  |  |
| 1 | No wash |  |  | 1 | 17.2 | 40.3 |  |  |  |
| 7 | Water | 1 | 15 | 1 | 11.6 |  | 11.4 | 73.2 | 189 |
| 8 | Water, pH = 4 | 1 | 15 | 1 | 11.4 | 24.3 | 13.9 | 71.7 | 216 |

According to the data in Table 1, pectin yield increased with increasing alcohol concentration in the wetting composition. This indicates that an alcohol concentration of at least 70% resulted in significantly less loss of pectin in the wash.

Table 1 also shows that the DE increased marginally with the alcohol concentration, and the molecular weight increased as the alcohol concentration increases from 70% to 96%. This indicates that the alcohol concentration was relevant to the loss of pectin during the washing, and that an alcohol concentration of at least about 70% to 96% may be desirable for some embodiments. In addition, Table 1 shows that without washing and pressing, peel dry matter is about 13%. With washing in plain water and with water at pH 4, dry matter is reduced to about 11%. When washing in alcohol followed by one pressing, the peel dry matter increases with the alcohol concentration up to about 20% when using 96% alcohol. In these experiments, washing in plain water and in water having pH 4 provided for about the same sugar concentration in the peel as washing with alcohol does. In both cases, the sugar concentration was reduced to about 22-25%.

Thus, these first experiments show that particularly the pectin yield is increased through washing with alcohol, and peel dry matter is substantially increased whereas residual sugar is marginally decreased compared to a regular washing with water.

Example 2

Effect of Number of Alcohol Wash

In this set of experiments, the number of alcohol washing steps was investigated.

TABLE 2

Dry Matter and Residual Sugar in Peel Being Washed Different Number of Times.

| Sample No. | Wetting Composition | No. wash | Wash Time Min. | No. press | Dry Matter of Pressed Peel % | Sugar Residual Sugar in the Peel % |
|---|---|---|---|---|---|---|
| 9 | 96% EtOH | 1 | 15 | 1 | 20.0 | 25.1 |
| 12 | 96% EtOH | 2 | 15 | 1 | 24.2 | 18.6 |
| 13 | 96% EtOH | 3 | 15 | 1 | 24.2 | 19.0 |
| 14 | 96% EtOH | 4 | 15 | 1 | 21.5 | 17.9 |

According to the data in Table 2, with 2-3 washes in 96% alcohol, the peel dry matter increased by about 20% after one pressing. 2-4 washings in 96% alcohol reduced the sugar concentration in the peel to about 18% or about 30% compared to washing once in 96% alcohol. Thus, 2-4 washings provided the highest dry matter and the lowest residual sugar concentration in the washed peel.

Example 3

Effect of Washing Time

Next, the washing time was investigated. Peel dry matter and residual sugar was recorded for peel being washing for different times in 96% alcohol followed by one pressing.

TABLE 3

Dry Matter and Residual Sugar in Peel Washed for Different Times.

| Sample No. | Wetting Composition | No. Wash | Wash Time Min. | Dry Matter Of Pressed Peel % | Sugar Residual Sugar in Peel % |
|---|---|---|---|---|---|
| 4 | 96% EtOH | 1 | 15 | 23.5 | 25.1 |
| 5 | 96% EtOH | 1 | 30 | 23.0 | 20.5 |

According to the data in Table 3, with one pressing, peel dry matter was unchanged when washing time was increased from 15 minutes to 30 minutes and residual sugar was decreased with increasing washing time. Thus, the data in Table 1 indicates that washing for about 30 minutes provided for high peel dry matter and low residual sugar in the peel.

Example 4

Effect of Washing Temperature

In the next experiments, peel was washed at different temperatures in 70% alcohol. After each wash of 60 minutes, the washed peel was pressed three times.

TABLE 4

Effects of Washing Temperature

| Sample No. | Biomass Slurry Liquid Temp. °C. | No. Wash | Wash Time min | No of Press | Dry Matter of Pressed Peel % | Residual Sugar in Peel Sugar % | Pectin Yield % | % DE | Mw KDalton of Pectin |
|---|---|---|---|---|---|---|---|---|---|
| 30 | 24 | 4 | 60 | 3 | 25.3 | 6.5 | 19.3 | 75.4 | 217 |
| 31 | 50 | 4 | 60 | 3 | 24.1 | 4.0 | 20.3 | 78.9 | 200 |

According to the data in Table 4, higher biomass slurry liquid temperature provided for a lower peel dry matter, and the peel dry matter was reduced by about 5% when washing temperature was increased from 24 to 50° C. In addition, with increasing washing temperature, the sugar concentration in the washed peel was reduced. The sugar level was reduced by about 40% when the washing temperature was increased from 24 to 50° C. The data in Table 4 also shows that the pectin yield was increased by about 5% when washing temperature was increased from 24 to 50° C., which may be a result of lower residual sugar. Furthermore, the DE of the resulting pectin appears to have been increased from about 75% to about 79% when the washing temperature was increased from 24 to 50° C. and, when the washing temperature was increased from 24 to 50° C., the molecular weight appears to have been reduced by about 8%. Thus, high washing temperature may favor a lower residual sugar level in the peel, a higher pectin yield and a higher DE, whereas low washing temperature may favor a higher molecular weight.

Example 5

Effect of pH in Wash

In the next set of experiments, fresh peel was washed in alcohol at different pH. The peel was washed four times and each time for one hour. After each wash, the washed peel was pressed three times.

TABLE 5

Effect of Wash at Different pH

| Sample No. | pH in Liquid Component of Biomass Slurry | No. wash | Wash Time min | No. press | Dry Matter of Pressed Peel % | Residual Sugar % in Pectin | Pectin Yield % | % DE of Pectin | Mw KDalton of Pectin |
|---|---|---|---|---|---|---|---|---|---|
| 26 | 1 | 4 | 60 | 3 | 24.6 | 5.0 | 16.5 | 75.8 | 238 |
| 27 | 4 | 4 | 60 | 3 | 25.5 | 6.1 | 17.8 | 75.7 | 252 |
| 28 | 7 | 4 | 60 | 3 | 24.8 | 5.8 | 17.0 | 75.7 | 259 |
| 29 | 10 | 4 | 60 | 3 | 25.0 | 6.9 | 15.2 | 68.4 | 180 |

The data in Table 5 shows that the peel dry matter was constant irrespective of the pH in the liquid component of the biomass slurry, whereas it appears that the sugar concentration in the washed peel increase with increasing pH of the liquid component of the biomass slurry. The sugar level was reduced by about 30% when the pH of the liquid component of the biomass slurry was reduced from pH 10 to pH 1. According to the data in Table 5, the pectin reached a maximum when washing was conducted in the pH range from about 4 to about 7. The pectin yield was about 15% lower at pH 10 than at pH 4. In the pH range from about 1 to about 7, DE was constant. However, as the pH was further increased to 10, the DE dropped by about 10%. The molecular weight of the resulting pectin stayed substantially constant after wash in the pH range from about 1 to about 7. However, as pH was further increased to 10, the molecular weight dropped about 30%. Thus, the data in Table 5 indicates that low pH favors low residual sugar in the peel, high pectin yield, high DE and high molecular weight of pectin.

Example 6

Effect of Number of Pressings

In the first set of these experiments, fresh peel was washed three times one hour in alcohol. After each washing, the washed peel was pressed once or twice. In the second set of these experiments, fresh peel was washed four times in alcohol and after each wash pressed once, twice and thrice.

TABLE 6

Effect of the Number of Pressings

| Sample No. | Wetting Comp. | No. Wash | Wash Time min | No. Press | Dry Matter of Pressed Peel % | Residual Sugar in Pectin % | Pectin Yield % | % DE of Pectin | Mw KDalton of Pectin |
|---|---|---|---|---|---|---|---|---|---|
| 18 | 70% EtOH | 3 | 60 | 1 | 18.8 | 6.8 | 21.6 | 71.2 | 237 |

TABLE 6-continued

Effect of the Number of Pressings

| Sample No. | Wetting Comp. | No. Wash | Wash Time min | No. Press | Dry Matter of Pressed Peel % | Residual Sugar in Pectin % | Pectin Yield % | % DE of Pectin | Mw KDalton of Pectin |
|---|---|---|---|---|---|---|---|---|---|
| 19 | 70% EtOH | 3 | 60 | 2 | 23.3 | 5.6 | 20.4 | 70.9 | 204 |
| 20 | 96% EtOH | 3 | 60 | 1 | 18.4 | 13.0 | 22.8 | 73.9 | 226 |
| 21 | 96% EtOH | 3 | 60 | 2 | 20.0 | 115 | 19.7 | 73.1 | 222 |
| 22 | 70% EtOH | 4 | 60 | 1 | 19.2 | 6.2 | 21.9 | 75.1 | 314 |
| 23 | 70% EtOH | 4 | 60 | 2 | 21.1 | 4.3 | 19.0 | 72.0 | 253 |
| 24 | 70% EtOH | 4 | 60 | 3 | 23.2 | 3.6 | 21.1 | 71.8 | 261 |

According to the data in Table 6, pressing twice increased the peel dry matter. However, it appears that twice pressing in 70% alcohol provided for the strongest increase in peel dry matter. Compared to a control in which peel was washed once and pressed once, three times washing with 70% ethanol and pressing twice after each wash increased dry matter from about 13% to about 24%, almost a doubling of the dry matter. The number of pressing steps did not change the sugar level much. However, 70% ethanol appears to have provided for the lowest sugar concentration in the washed and pressed peel. The data in Table 6 indicates that pressing twice results in a slight decrease in pectin yield. The DE of the resulting pectin was hardly affected by the number of pressings. This data may indicate a tendency for washing in 96% ethanol to provide for slightly higher DE. In addition, the data in Table 6 seems to indicate a tendency for the molecular weight to drop as the number of pressings increase. This tendency was more pronounced for washing in 70% alcohol than in 96% alcohol.

Thus, the first set of experiments indicated that the number of pressings favors a higher peel dry matter and to some extent the amount of residual sugar. However, a lowered strength alcohol appears to have had a stronger effect. On the other hand, the number of pressings seems to have favored a marginal lower DE and molecular weight.

The data in Tables 5 and 6 show that there does not seem to be a major difference in peel dry matter whether the peel is washed three or four times and pressed two or three times. However, the lowest concentration of sugar in the washed peel was accomplished using four washes and three pressings after each wash. Furthermore, the data in Tables 5 and 6 show the number of washing and number of pressings had no major effect on pectin yield, a tendency for slightly lower yield as the number of pressings was increased, and the DE of the resulting pectin stayed unchanged as the number of washings and the number of pressings was increased.

The data in Table 6 shows that four washings provided higher molecular weight and pressing once provided higher molecular weight. Thus, this second set of experiments indicate that more washing and higher number of pressings favor a lower residual sugar level in the peel, whereas more washing and low number of pressings favor a higher molecular weight of the resulting pectin. The data in Tables 5 and 6 also indicate that the peel dry matter, the pectin yield and the DE of the resulting pectin appear to be unaffected by more washing steps and a higher number of pressings.

Example 7

Effect of Pressing Time

In these experiments the number of alcohol washings was four, and after each pressing, the pressing time was set to various times ranging from 0 seconds and up to 600 seconds.

TABLE 7

Effect of Pressing Time

| Sample No. | Wetting Comp. | No. Wash | Wash Time min | No. Press | Press Time Sec. | Dry Matter of Pressed Peel % | Residual Sugar % in Pectin | Pectin Yield % | % DE of Pectin | Mw KDalton of Pectin |
|---|---|---|---|---|---|---|---|---|---|---|
| 43 | 70% IPA | 4 | 60 | 3 | 0 0 0 | 25.6 | 6.4 | 18.2 | 76.8 | 206 |
| 44 | 70% IPA | 4 | 60 | 1 | 60 | 24.3 | 8.0 | 20.2 | 74.9 | 251 |
| 45 | 70% IPA | 4 | 60 | 2 | 60 60 | 27.7 | 7.2 | 20.2 | 73.4 | 245 |
| 46 | 70% IPA | 4 | 60 | 1 | 180 | 25.9 | 7.5 | 18.3 | 76.7 | 262 |
| 47 | 70% IPA | 4 | 60 | 2 | 180 600 | 34.7 | 7.2 | 17.9 | 76.9 | 215 |
| 54 | 70% | 4 | 60 | 3 | 180 | 37.7 | 5.1 | 18.5 | 76.0 | 203 |

TABLE 7-continued

Effect of Pressing Time

| Sample No. | Wetting Comp. | No. Wash | Wash Time min | No. Press | Press Time Sec. | Dry Matter of Pressed Peel % | Residual Sugar % in Pectin | Pectin Yield % | % DE of Pectin | Mw KDalton of Pectin |
|---|---|---|---|---|---|---|---|---|---|---|
|  | IPA |  |  |  | 600 |  |  |  |  |  |
|  |  |  |  |  | 600 |  |  |  |  |  |
| 52 | 70% EtOH | 4 | 60 | 3 | 180 | 35.0 | 5.0 | 17.7 | 77.1 | 269 |
|  |  |  |  |  | 600 |  |  |  |  |  |
|  |  |  |  |  | 600 |  |  |  |  |  |

The data in Table 7 shows that when peel was pressed once, but with a holding time of 60 seconds, the dry matter was about the same as for peel being pressed three times, but without holding time. As the holding time was increased, the peel dry matter increased, and the peel dry matter using a triple pressing with holding times 180 seconds, 600 seconds and 600 seconds, respectively, provided for the highest peel dry matter, about 37%, which was about three times the value of peel washed in water and pressed once without holding time. With ethanol, the dry matter of the peel was almost as high as with IPA.

The data featured in Table 7 indicates that the sugar level was generally low, but there seemed to be an advantage in pressing with total holding time of about 20 minutes the same result was observed with ethanol.

According to the data in Table 7, both pectin yield and DE of the resulting pectin appeared to be independent of the pressing time. In the Examples featured in Table 7 with IPA, molecular weight appeared to be highest when pressing times were no more than about 180 seconds. As the total pressing time increased, the molecular weight decreased. However, with ethanol, the molecular weight remained high even at the long total pressing times.

Thus, the data in Table 7 indicates that pressing time favored high peel dry matter and low residual sugar, whereas pressing time did not influence pectin yield and DE of the resulting pectin.

In the Examples featured in Table 7, there appeared to be a tendency of lower molecular weight of the resulting pectin when washing was done with IPA and pressing time exceeded 180 seconds. However, with ethanol, high molecular weight seemed to be favored by longer pressing times.

Example 8

Effect of Pressure During Pressing

In order to indicate the effect of the pressure used during pressing, two tests were made. One with a load cell allowing for a pressure of 25 kg. and a load cell allowing for a pressure of 50 kg.

TABLE 8

Effect of Pressure During Pressing

| Sample No. | Wett. Comp. | Load Cell Kg | No. Wash | Wash Time Min | No. Press | Pressing Time sec | Dry Matter Of Pressed Peel % | Residual Sugar % in Pectin | Pectin Yield % of Pectin | % DE of Pectin |
|---|---|---|---|---|---|---|---|---|---|---|
| 57 | 70% EtOH | 25 | 4 | 60 | 3 | 60 | 32.2 | 3.9 | 20.7 | 74.6 |
|  |  |  |  |  |  | 300 |  |  |  |  |
|  |  |  |  |  |  | 180 |  |  |  |  |
| 58 | 70% EtOH | 50 | 4 | 60 | 3 | 60 | 34.1 | 4.3 | 18.4 | 70.7 |
|  |  |  |  |  |  | 300 |  |  |  |  |
|  |  |  |  |  |  | 180 |  |  |  |  |

In the Examples featured in Table 8, increasing pressure provided for at best a marginal increase in peel dry matter, whereas it seems that higher pressure led to somewhat higher sugar concentration. In addition, higher pressure seemed to lead to a somewhat lower pectin yield. However, the yield was comparable with previous findings. A slight decrease in DE was observed at high pressure, but both DE values were within the previous findings.

Example 9

Effect of Alcohol Type

In this set of experiments, the difference between IPA and ethanol was further investigated. In the case of IPA, four independent tests were conducted.

TABLE 9

Effect of Alcohol Type

| Sample No. | Wetting Comp. | No. Wash | Wash Time Min | No. Press | Dry Matter Of Pressed Peel % | Sugar % | Pectin Yield % | % DE | Mw KDalton of Pectin |
|---|---|---|---|---|---|---|---|---|---|
| 39 | 70% IPA | 4 | 60 | 3 | 28.3 | 12.4 | 17.8 | 70.9 | 185 |
| 40 | 70% IPA | 4 | 60 | 3 | 26.4 | 6.7 | 18.3 | 73.9 | 196 |
| 41 | 70% IPA | 4 | 60 | 3 | 26.5 | 6.9 | 17.7 | 75.5 | 205 |
| 42 | 70% IPA | 4 | 60 | 3 | 26.7 | 6.2 | 19.7 | 75.5 | 195 |
| 43 | 70% IPA | 4 | 60 | 3 | 25.6 | 6.4 | 18.2 | 76.8 | 206 |
|  | IPA average |  |  |  | 26.7 | 7.7 | 18.3 | 74.5 | 197 |
| 30 | 70% EtOH | 4 | 60 | 3 | 25.3 | 6.5 | 19.3 | 75.4 | 217 |

In the data featured in Table 9, when using IPA, the peel dry matter increased by about 5% compared to ethanol. However, sugar concentration was about 15% lower when using ethanol compared to IPA. Ethanol appeared to provide for a slightly higher yield, about 5% and a marginally higher DE. Ethanol appeared to provide for higher molecular weight—about 10%. Thus, in Example 9, ethanol favored higher pectin yield and higher pectin molecular weight, whereas IPA favored higher peel dry matter and lower residual sugar.

Example 10

Comparison of Lemon and Orange

A comparison of the various treatments performed on lemon and orange peel was made.

TABLE 10

Comparison of Lemon and Orange

| Sample No. | Peel | Wetting Comp. | No. Wash | Wash Time Min | No. Press | Dry Matter Of Pressed Peel % | Reduced Sugar % in Pectin | Pectin Yield % | % DE of Pectin |
|---|---|---|---|---|---|---|---|---|---|
| 1 | Lemon | No wash |  |  | 1 | 17.2 | 40.3 | 9.5 | 73.7 |
| 17 | Lemon | Water - pH = 4 | 2 | 15 | 1 | 10.1 | 19.8 | 18.8 | 72.5 |
| 24 | Lemon | 70% EtOH | 4 | 60 | 3 | 23.2 | 3.6 | 21.2 | 71.8 |
| 49 | Orange | No wash | 0 |  | 1 | 20.9 | 40.4 | 7.5 | 73.0 |
| 50 | Orange | Water - pH = 4 | 2 | 15 | 1 | 10.7 | 23.1 | 14.9 | 73.6 |
| 51 | Orange | 70% EtOH | 4 | 60 | 3 | 24.0 | 6.2 | 18.9 | 74.8 |

In the data featured in Table 10, the dry matter was reduced markedly when washing was conducted at pH 4, washing in 70% ethanol and pressing three times after each wash increased the dry matter, the dry matter became higher in orange compared with lemon, washing and pressing greatly reduced sugar concentration, and the ethanol wash and pressing was very effective. In addition, the pectin yield increased with washing and was highest for the peel having been washed with ethanol, however, the DE was unaffected.

The foregoing laboratory Scale-Examples indicated:

With respect to alcohol strength, the pectin yield was increased when the alcohol strength was 70% by weight of the wetting composition or higher. Peel dry matter was substantially increased and residual sugar was marginally decreased compared to washing with water. The number of washing steps had a substantial effect, and 2-4 washing steps appeared to be the optimal number of washing steps to provide for the highest dry matter in the peel and the lowest residual sugar concentration in the washed peel. Washing time also played a role, and the optimum washing time appeared to be about 30 minutes to provide for high peel dry matter and low residual sugar level in the peel. High washing temperature seemed to favor a lower residual sugar level in the peel, a higher pectin yield and a higher DE of the resulting pectin. However, low washing temperature appeared to favor a higher molecular weight of the resulting pectin. Low pH favored low residual sugar in the peel, high pectin yield, high DE of the resulting pectin and high molecular weight of the resulting pectin. The number of pressings after wash seemed to favor a higher peel dry matter and to a lesser extent the residual sugar level. However, when combining number of pressing with number of washing steps, the residual sugar was reduced while the peel dry matter stayed substantially constant. The pressing time favored high peel dry matter and low residual sugar, but did not influence the pectin yield or the DE of the resulting pectin. Using a three step washing in 70% alcohol combined with a triple pressing with holding times of 180+600+600 seconds, the peel dry matter was increased three fold to 37%. The pressure during pressing appeared to have no substantial impact and the same appeared to be true when the volume of wash liquid was doubled. With respect to the alcohol type, ethanol appeared to favor marginally higher pectin yield and marginally higher pectin molecular weight, whereas isopropanol favored marginally higher peel dry matter and lower residual sugar. Thus, ethanol and isopropanol could be used interchangeably. With respect to pectin starting material, lemon and orange behaved about the same. According to these laboratory experiments, a particularly desirable embodiment appears to be a process in which fresh peel is washed three times in 70% alcohol at room temperature, each washing step is conducted for 30 minutes and after each wash, the washed peel is pressed three times at 4-8 bar, each pressing time being maintained for about 200-600 seconds.

The next examples were made to validate the laboratory findings in pilot plant scale and to evaluate the concept of using a countercurrent alcohol wash with one single pressing step after the washing.

Example 12

Consecutive Washing and Pressing of Fresh Peel in Pilot Plant

In the Example 12, freshly juiced orange peel was used as the starting material and for pressing, a screw type press was used.

The results from the washing and pressing experiments are listed in Table 11. After each pressing, fresh 80% IPA was added for the following wash.

Example 11

Results of Washing with IPA Followed by Pressing

| Sample | Comment | Peel Dry Matter % | % IPA Density | Peel Kg | IPA Spent Liter | IPA Added Liter | Centrifuged Impurities In IPA % | Pectin Yield % |
|---|---|---|---|---|---|---|---|---|
| 1151-104-1 | Fresh peel | 22.4 | | 117 | | 129.5 | | |
| 1151-104-2 | Fresh peel + IPA | 22.3 | | | | | | |
| 1151-104-3 | 1. press | 23.8 | 52 | 66 | 135 | 121.2 | 4 | 13.3 |
| 1151-104-4 | 2. press | 35.6 | 68 | 25.7 | 170 | 35 | 2 | |
| 1151-104-5 | 3. press | 50.5 | | 15.6 | 50 | 30 | 3 | 34.2 |
| 1151-104-6 | 4. press | 57.6 | 78 | 11.2 | 45 | 30 | 4 | 36.4 |
| 1151-104-7 | 5. press | 59.5 | 80 | 8.7 | 35 | 30 | 4 | 31.9 |
| 1151-104-8 | 6. press | 56.0 | 80 | 7.5 | 35 | | 5 | |
| 1151-104-9 | 7. press | 50.3 | 80 | 8.0 | 30 | | 5 | |

Table 12 shows the results from laboratory analysis. As a measure for molecular weight, the intrinsic viscosity was chosen.

TABLE 12

Laboratory Analysis

| Sample | Residual Sugar in Peel % | Pectin DE % | Pectin GA % | Pectin IV dl/g | Clarity Cold % T | Clarity Warm % T | pH 1% |
|---|---|---|---|---|---|---|---|
| 1151-104-3 | 33.3 | 62.5 | 81.6 | 4.836 | 67.4 | 78.0 | 3.15 |
| 1151-104-4 | 21.1 | | | | | | |
| 1151-104-5 | 13.9 | 63.8 | 81.9 | 5.094 | 85.1 | 87.0 | 3.46 |
| 1151-104-6 | 11.8 | 65.0 | 81.3 | 5.124 | 35.9 | 82.4 | 3.62 |
| 1151-104-7 | 10.4 | 63.4 | 79.9 | 4.926 | 42.2 | 81.9 | 3.33 |
| 1151-104-8 | 9.6 | | | | | | |
| 1151-104-9 | 9.4 | | | | | | |

The data featured in Tables 11 and 12 indicate that washing and pressing 4-6 times increased the peel dry matter to above 50% by weight of the peel, and at those washings and pressings, the IPA concentration in the spent IPA was constant at about 80% by weight of the wetting composition. In addition, the pectin yield was increased to above 30%. In addition, after about 5 pressings, the residual sugar level in the pressed peel fell to about 10%. Furthermore, in data featured in Tables 11 and 12, the DE, GA and IV (molecular weight) of the resulting pectin products were fairly constant irrespective of the number of washings and pressings. In addition, these are all within normal range, which may indicate that the high pectin yield is not caused by impurities. However, the clarity of cold solution of the resulting pectin products appeared to be decreasing as the number of washings and pressings were increased, whereas the clarity of warm pectin solutions remained high.

This could be due to the increased maceration of the peel with increased number of pressings. Still, the impurities appeared to be soluble hot. This could have indicated that the low clarity might be a result of the fruit used in the examples being waxed.

Thus, the Examples featured in Tables 11 and 12 showed that when using a screw type press, substantially higher peel dry matter was achievable compared to the hydraulic type press used in the laboratory experiments. These examples also verified pressing time as an important factor. The screw type press used in these examples ran with about 20 rpm, which corresponded to a run through time of about 10-15 minutes.

Example 11

Four Steps Countercurrent Wash with Isopropanol in Pilot Plant

The results from washing of peel are listed in Table 13.

TABLE 13

Washing Time and Density of IPA

| Washing Time Minutes | Density of IPA g/ml |
|---|---|
| 5 | 0.880 |
| 10 | 0.890 |

TABLE 13-continued

Washing Time and Density of IPA

| Washing Time Minutes | Density of IPA g/ml |
|---|---|
| 15 | 0.895 |
| 20 | 0.895 |

The results from washing and pressing are listed in Table 14.

TABLE 14

Results of Countercurrent Wash and Pressing

| Sample | Peel Kg. | IPA Kg. | IPA Density % | IPA GC % | Peel Dry Matter % | Pectin Yield % |
|---|---|---|---|---|---|---|
| 1151-105-0 | | | | | 20.1 | 2.3 |
| 1151-105-A1 | 21.2 | 27.0 | 54 | 46.12 | 18.5 | |
| 1151-105-A2 | 18.7 | 25.2 | 70 | 58.08 | 18.0 | |
| 1151-105-A3 | 18.2 | 23.8 | 78 | 63.34 | 20.6 | |
| 1151-105-A4 | 18.1 | 21.7 | 79 | 60.77 | 21.2 | |
| 1151-105-A-press | 3.9 | 31.7 | 78 | 60.76 | 39.4 | 28.8 |
| 1151-105-B1 | 20.5 | 23.0 | 42 | 36.63 | 17.4 | |
| 1151-105-B2 | 19.9 | 19.5 | 62 | 51.94 | 27.6 | |
| 1151-105-B3 | 18.8 | 32.2 | 70 | 50.99 | 27.6 | |
| 1151-105-B4 | 18.4 | 21.6 | 77 | 63.95 | 30.0 | |
| 1151-105-B-press | 2.0 | 24.0 | 78 | 63.95 | 54.4 | 31.2 |
| 1151-105-C1 | 20.0 | 21.2 | 36 | 35.08 | 21.3 | |
| 1151-105-C2 | 18.1 | 32.6 | 70 | 48.09 | 27.8 | |
| 1151-105-C3 | 17.4 | 35.4 | 74 | 55.29 | 24.9 | |
| 1151-105-C4 | 15.9 | 18.1 | 78 | 60.08 | 26.4 | |
| 1151-105-C-press | 3.6 | 34.8 | 78 | 60.08 | 46.8 | 29.3 |
| 1151-105-D1 | 21.2 | 32.0 | 42 | 35.28 | 27.2 | |
| 1151-105-D2 | 19.9 | 37.3 | 62 | 45.21 | 25.5 | |
| 1151-105-D3 | 19.1 | 34.5 | 70 | 51.80 | 27.4 | |
| 1151-105-D4 | 18.5 | 21.4 | 78 | 58.61 | 29.6 | |
| 1151-105-D-press | 4.4 | 40.8 | 76 | 58.47 | 46.2 | 28.3 |
| 1151-105-E1 | 20.4 | 33.9 | 42 | 33.38 | 24.5 | |
| 1151-105-E2 | 19.2 | 33.8 | 58 | 43.68 | 26.9 | |
| 1151-105-E3 | 17.8 | 35.5 | 70 | 53.15 | 23.9 | |
| 1151-105-E4 | 17.3 | 32.0 | 78 | 62.89 | 26.4 | |
| 1151-105E-press | 3.8 | 36.0 | 76 | 62.80 | 48.6 | 28.1 |

Table 15 lists the laboratory analysis of the resulting pectin products from each step in the countercurrent wash and pressing.

TABLE 15

Analysis of Resulting Pectin Products

| Pectin | Residual Sugar % | Mw KDalton | IV dl/g | DE % | GA % | Clarity Cold % T | Clarity Hot % T | pH | CS + $Ca^{2+}$ cP | CS − $Ca^{2+}$ cP |
|---|---|---|---|---|---|---|---|---|---|---|
| 1151-105-0 | 16.05 | 301 | 5.458 | 60.8 | 81.3 | 32.0 | 30.1 | 3.13 | 22.9 | 11.8 |
| 1151-105-A | 15.25 | 303 | 5.184 | 65.8 | 80.2 | 14.4 | 15.3 | 3.16 | | |
| 1151-105-B | 14.55 | 291 | 5.177 | 66.1 | 80.0 | 13.6 | 13.3 | 3.13 | | |
| 1151-105-C | 15.24 | 255 | 4.359 | 65.4 | 79.6 | 13.2 | 13.2 | 3.17 | | |
| 1151-105-D | 13.08 | 288 | 5.270 | 63.5 | 83.1 | 87.3 | 89.6 | 3.36 | | |
| 1151-105-E | 16.05 | 268 | 4.917 | 65.5 | 81.7 | 15.4 | 16.0 | 3.08 | 53.5 | 13.5 |

The theoretical mass balance is listed in Table 16.

TABLE 16

Theorectical Mass Balance According to the E-Series

| Step | Peel Kg | IPA Wash Kg | IPA Spent Kg | Peel After Kg |
|---|---|---|---|---|
| Start | 20.0 | | | 20.0 |
| First wash | 20.0 | 40.6 | 40.2 | 20.4 |
| Second wash | 20.4 | 39.4 | 40.6 | 19.2 |
| Third wash | 19.2 | 38.0 | 39.4 | 17.8 |
| Fourth wash | 17.8 | 24.0 | 38.0 | 17.3 |
| Press | 17.3 | | 13.5 | 3.8 |

A mass balance according to the E-series:

TABLE 17

Mass Balance of Countercurrent Wash

| Step | Peel Kg | IPA Wash Kg | IPA Wash % | IPA Spent Kg | IPA Spent % | Peel After Kg | Peel Dry Matter % | Pectin Yield % |
|---|---|---|---|---|---|---|---|---|
| Start | 20.0 | | | | | 20.0 | 20.1 | 2.3 |
| First wash | 20.0 | 37.3 | 45.21 | 33.9 | 33.38 | 20.4 | 24.5 | |
| Second wash | 20.4 | 34.5 | 51.80 | 33.8 | 43.68 | 19.2 | 26.9 | |
| Third wash | 19.2 | 40.8 | 58.61 | 35.5 | 53.15 | 17.8 | 23.9 | |
| Fourth wash | 17.8 | 24.0 | 80.00 | 36.0 | 62.80 | 17.3 | 26.4 | |
| Press | 17.3 | | | | | 3.8 | 48.6 | 28.1 |

Similarly, a mass balance according to the D-series:

TABLE 18

Mass Balance of Countercurrent Wash

| Step | Peel Kg | IPA Wetting Comp. Kg | IPA Wetting Comp. % | IPA Spent Kg | IPA Spent % | Peel After Kg | Peel Dry Matter % | Pectin Yield % |
|---|---|---|---|---|---|---|---|---|
| Start | 20.0 | | | | | 20.0 | 20.1 | 2.3 |
| First wash | 20.0 | 32.6 | 48.01 | 32.0 | 35.28 | 21.2 | 27.2 | |

TABLE 18-continued

Mass Balance of Countercurrent Wash

| Step | Peel Kg | IPA Wetting Comp. Kg | IPA Wetting Comp. % | IPA Spent Kg | IPA Spent % | Peel After Kg | Peel Dry Matter % | Pectin Yield % |
|---|---|---|---|---|---|---|---|---|
| Second wash | 21.2 | 35.4 | 55.29 | 37.3 | 45.21 | 19.9 | 25.5 | |
| Third wash | 19.9 | 34.8 | 60.08 | 35.4 | 51.80 | 19.1 | 27.4 | |
| Fourth wash | 19.1 | 24.0 | 80.00 | 40.8 | 58.47 | 18.5 | 29.6 | |
| Press | 18.5 | | | | | 4.4 | 46.2 | 28.3 |

FIG. 1 shows a mass balance of series E and shows that there is a good correlation between the IPA concentration in the spent liquid component from the biomass slurry and the IPA concentration in the prior incoming IPA wetting composition. Also, the amounts of liquid component from the biomass slurry being used in the prior washing step correlate reasonably well with the spent liquid component from the subsequent washing step. However, the actual data did not equal the theoretical values. This may reflect the fact that these were some losses during the process, so the scale may have been too small. Thus, the countercurrent scheme used in these experiments did provide for a reasonable steady state system in which the countercurrent wash results in about 4 kg peel with a dry matter of about 28% by weight of the peel and a spent amount of alcohol for distillation amounting to about 35 kg having an IPA concentration of about 34%. Energy wise, the spent IPA to be distilled comes from the IPA in the pressed peel and the spent IPA from the first wash. After pressing, 3.8 kg wet peel is produced, which correspond to 1.846 kg dry peel and 1.954 kg IPA. The IPA has a strength of 62.8% by weight of the wetting composition which translates into 1.227 kg IPA. Theoretically, spent IPA in the first wash is the IPA being led into wash No. 4, namely 24 kg with a strength of 80% or 19.2 kg IPA minus the IPA leaving with the pressed peel. Thus, the amount of IPA to be distilled is 17.973 kg. Theoretically, the amount of IPA leaving from wash No. 1 is the amount IPA coming from Wash. No. 2 minus the IPA leaving with the washed peel. This amounts to 40.2 kg, which translates into this IPA having a strength 45%, which is somewhat higher than the actual measurement of 33.4%. In order to calculate the energy consumption, one has to make the assumption that the IPA going into wash No. 4 is not 24 kg. but only 15 kg. In this case, the spent IPA in wash No. 1 becomes 31.2 kg with a strength of 34.5%, which is close to the actual measurements.

The following tables show the energy consumption of an alcohol washing process in accordance with an embodiment of this invention and the conventional drying process.

TABLE 19

Energy Consumption of Alcohol Washing Process
Alcohol Process

| | MT/MT Peel |
|---|---|
| Wet Peel | 9 |
| Water | 0 |
| Effluent | 8 |
| Steam | 2.52 |
| Steam cost R$/MT | 45 |
| Energy cost R$/MT Peel | 113 |
| Energy cost US$/MT Peel | 49 |
| Pectin Yield | 25% |
| Pectin MT/MT Peel | 0.250 |
| Specific energy cost R$/MT Pectin | 453 |
| Specific energy cost US$/MT Pectin | 197 |

TABLE 20

Energy Consumption of Conventional Drying Process
Conventional Drying Process

| | MT/MT Peel | NM3/MT Peel |
|---|---|---|
| Wet Peel | 9 | |
| Water | 23 | |
| Effluent | 32 | |
| Nat Gas | | 524 |
| Nat Gas cost R$/NM3 | | 1.45 |
| Energy cost R$/MT Peel | | 760 |
| Energy cost US$/MT Peel | | 330 |
| Pectin Yield | 25% | |
| Pectin MT/MT Peel | 0.250 | |
| Specific energy cost R$/MT Pectin | | 3040 |
| Specific energy cost US$/MT Pectin | | 1322 |

TABLE 21

Savings When Using Alcohol Washing Process
Savings

| | MT/MT Peel |
|---|---|
| Wet Peel | 0 |
| Water | 23 |
| Effluent | 24 |
| Energy cost R$/MT Peel | 647 |
| Energy cost US$/MT Peel | 281 |
| Specific energy cost R$/MT Pectin | 2587 |
| Specific energy cost US$/MT Pectin | 1125 |

As shown in Tables 19-21, per 1 mT dry peel, an alcohol washing and pressing process according to an embodiment of this invention reduces the energy cost by about 280 USD per mT dry peel. In addition, the alcohol process in accordance with an embodiment of this invention saves on water consumption and effluent and reduces the amount of $CO_2$ emitted by about 1 mT $CO_2$ per 1 mT produced dry peel. With respect to the pectin quality, there seemed to be a tendency of higher DE in pectin having been subjected to the alcohol washing process. As previously observed, the clarity appeared to suffer during the alcohol washing process. Thus, since this work applies only one pressing, the amount of fines was substantially less than what was observed with a process involving consecutive washing and pressing. Without being bound of theory, it is expected that the lack of clarity was caused by the fact that the starting material was peel from fresh oranges destined to be eaten as fresh fruit. Such fruit is conventionally waxed, and it is suspected that the wax is the cause of lower clarity. In addition, galacturonic acid was high, which indicated a pure pectin, and the washing with alcohol removed substantial amounts of sugar from the fresh peel.

Example 13

Four Steps Countercurrent Wash with Ethanol in Pilot Plant

A countercurrent experiment was performed with ethanol instead of isopropanol.

Table 22 shows the data from the washing and pressing scheme.

TABLE 22

Results of Countercurrent Wash and Pressing.

| Sample | Peel Kg | EtOH Kg | EtOH Density % | EtOH GC % | Peel Dry Matter % | Pectin Yield % |
|---|---|---|---|---|---|---|
| 1151-106-0 | | | | | 22.6 | 31.2 |
| 1151-106-A1 | 22.4 | 28.1 | 46 | | 27.0 | |
| 1151-106-A2 | 21.6 | 26.5 | 64 | 56.38 | 28.9 | |
| 1151-106-A3 | 20.9 | 25.1 | 70 | 66.09 | 26.9 | |
| 1151-106-A4 | 18.7 | 25.2 | | 64.65 | 25.7 | |
| 1151-106-A-press | 5.5 | 37.5 | 70 | 66.11 | 51.6 | 31.2 |
| 1151-106-B1 | 23.2 | 28.8 | 48 | 50.38 | 29.0 | |
| 1151-106-B2 | 22.8 | 24.6 | 60 | 55.94 | 33.6 | |
| 1151-106-B3 | 21.7 | 37.6 | 66 | 58.41 | 27.3 | |
| 1151-106-B4 | 21.3 | 263 | 72 | 68.51 | 24.2 | |
| 1151-106-B-press | 5.9 | 40.0 | 70 | 63.39 | 46.8 | 31.1 |
| 1151-106-C1 | 25.2 | 18.8 | 24 | 34.35 | 30.5 | |
| 1151-106-C2 | 23.3 | 39.4 | 24 | 48.97 | 28.0 | |
| 1151-106-C3 | 22.1 | 38.5 | 58 | 58.47 | 25.7 | |
| 1151-106-C4 | 20.9 | 28.6 | 68 | 61.79 | 27.1 | |
| 1151-106-C-press | 6.4 | 53.6 | 66 | 60.21 | 45.4 | 32.0 |
| 1151-106-D1 | 25.5 | 32.5 | 32 | 34.60 | 24.8 | |
| 1151-106-D2 | 24.9 | 39.4 | 56 | 49.72 | 25.2 | |
| 1151-106-D3 | 22.8 | 43.5 | | 56.18 | 24.7 | |
| 1151-106-D4 | 21.7 | 25.4 | 70 | 61.74 | 26.1 | |
| 1151-106-D-press | 4.6 | 40.8 | 68 | 60.20 | 45.0 | 31.9 |
| 1151-106-E1 | 25.3 | 33.5 | 34 | 37.41 | 25.5 | |
| 1151-106-E2 | 24.4 | 43.5 | 54 | 47.69 | 27.7 | |
| 1151-106-E3 | 22.0 | 41.1 | 64 | 55.55 | 29.4 | |
| 1151-106-E4 | 21.2 | 21.8 | 70 | 61.15 | 24.2 | |
| 1151-106-E-press | 4.5 | 37.5 | 68 | 60.58 | 60.3 | 34.4 |

Note:
Extraction made on dried peel.

Table 23 lists the laboratory analysis of the resulting pectin products from each step in the countercurrent wash and pressing.

TABLE 23

Analysis of Resulting Pectin Products

| Pectin | Residual Sugar % | Mw KDalton | IV dl/g | DE % | GA % | Clarity Cold % T | Clarity Hot % T | pH | CS + $Ca^{2+}$ cP | CS − $Ca^{2+}$ cP |
|---|---|---|---|---|---|---|---|---|---|---|
| 1151-106-0 | 39.7 | 267 | 5.262 | 66.4 | 80.7 | 71.4 | 70.7 | 3.27 | 65.5 | 14.6 |
| 1151-106-A | 7.9 | 306 | 5.877 | 68.6 | 79.4 | 73.2 | 89.9 | 3.46 | | |
| 1151-106-B | 9.5 | 350 | 6.143 | 67.7 | 78.8 | 72.4 | 89.5 | 3.56 | | |
| 1151-106-C | 10.6 | 346 | 6.016 | 67.5 | 79.8 | 77.7 | 90.4 | 3.39 | | |
| 1151-106-D | 9.8 | 243 | 4.555 | 67.3 | 80.5 | 47.4 | 86.0 | 3.49 | | |
| 1151-106-E | 9.3 | 271 | 5.769 | 69.1 | 82.7 | 86,.1 | 87.3 | 3.42 | 34.0 | 16.6 |

The theoretical mass balance is listed in Table 24.

TABLE 24

Theoretical Mass Balance According to the E-series

| Step | Peel Kg | EtOH Wett. Comp. Kg | EtOH Spent Kg | Peel After Kg |
|---|---|---|---|---|
| Start | 20.0 | | | 22.4 |
| First wash | 20.0 | 44.8 | 33.5 | 25.3 |
| Second wash | 25.3 | 43.9 | 44.8 | 24.4 |
| Third wash | 24.4 | 41.5 | 43.9 | 22.0 |
| Fourth wash | 22.0 | 24.0 | 24.8 | 21.2 |
| Press | 21.2 | | 16.7 | 4.5 |

A Mass balance according to the E-series:

TABLE 25

Mass Balance of Countercurrent Wash

| Step | Peel Kg | EtOH Wett. Comp. Kg | EtOH Wash % | EtOH Spent Kg | EtOH Spent % | Peel After Kg | Peel Dry Matter % | Pectin Yield % |
|---|---|---|---|---|---|---|---|---|
| Start | 20.0 | | | | | 20.0 | 22.6 | 31.3 |
| First wash | 20.0 | 43.5 | 47.69 | 33.5 | 37.41 | 25.3 | 25.5 | |
| Second wash | 25.3 | 41.1 | 55.55 | 43.5 | 47.69 | 24.4 | 27.7 | |
| Third wash | 24.4 | 37.5 | 60.58 | 41.1 | 55.55 | 22.0 | 29.4 | |
| Fourth wash | 22.0 | 24.0 | 80.00 | 15.7 | 61.15 | 21.2 | 24.2 | |
| Press | 21.2 | | | 21.8 | 60.58 | 4.50 | 60.3 | 34.4 |

FIG. 2 shows the mass balance according to the E-series and there was a pretty good correlation between the theoretical mass balance and the actual one.

From an energy saving point of view, the cost saving is the same as was found in the experiments with iso propanol, which also means that the emission of $CO_2$ is reduced to the same level as washing with iso propanol. With respect to the quality of the resulting pectin, it is as a minimum on par with the pectin quality of the resulting pectin from the non-alcohol washed peel. The ethanol wash seemed to have provided for a pectin product with a higher molecular weight as measured by intrinsic viscosity, a higher DE, and a higher pectin purity as measured by the galacturonic acid. Additionally, washing with ethanol increases the clarity of the resulting pectin's clarity in solution. Further, the calcium sensitivity of the pectin appears to be somewhat reduced through washing with ethanol, however, this may very well be within experimental error.

Example 14

Two Steps Countercurrent Wash with Ethanol in Pilot Plant

The Examples 12 and 13 show that washing with alcohol and subsequent pressing once provides for a substantial energy saving in the following drying of the washed and pressed polymer containing material. They also show that the resulting quality of the polymer when extracted from the washed, pressed and dried material remains at least on par with the polymer resulting from extraction of the same material as is, i.e. the material not being washed and pressed.

Table 26 shows the result from the pilot plant experiment with a two step countercurrent wash followed by a pressing.

TABLE 26

Results of Countercurrent Wash and Pressing

| Sample | Peel Kg | EtOH Kg | EtOH Density % | Peel Dry Matter % | Pectin Yield % |
|---|---|---|---|---|---|
| 1151-109-0 | | | | 20.0 | 18.3 |
| 1151-109-A3 | 22.0 | 20.8 | 48 | 27.2 | |
| 1151-109-A4 | 21.7 | 25.1 | 66 | 27.4 | |
| 1151-109-A-press | 4.8 | 39.3 | 62 | 55.0 | 33.9 |
| 1151-109-B3 | 21.9 | 35.0 | 44 | 54.6 | |
| 1151-109-B4 | 20.3 | 26.2 | 65 | 26.6 | |
| 1151-109-B-press | 5.1 | 38.9 | 75 | 57.6 | 32.2 |
| 1151-109-C3 | 21.6 | 32.8 | 39 | 26.0 | |
| 1151-109-C4 | 18.7 | 26.0 | 62 | 27.3 | |
| 1151-109-C-press | 4.9 | 38.0 | 61 | 58.2 | 33.8 |

According to the Examples 12-14, the peel dry matter after pressing was about 60%, which was the same as the peel dry matter using a four step washing scheme, so it is was possible to achieve the energy savings using a two step countercurrent washing followed by pressing once. Thus, Examples 12-14 showed that using a countercurrent washing scheme consisting of 2-4 washing steps provided for high pectin yield even with alcohol concentrations in the washings in the range from about 45% to about 80%. In addition, such countercurrent washing scheme provided for a pectin product which was at least on par with the pectin product being extracted from peel, which has not undergone such countercurrent wash.

Example 15

Four Steps Countercurrent Wash of Pectin Waste with Isopropanol in Pilot Plant

Another example of a polymer containing material is the waste material from the pectin production. Such waste is traditionally used for cattle feed, and this example was done to evaluate the alcohol washing and pressing process to establish if this process would lead to a waste product, which has enough dry matter to be combustible. Results from the experiment are listed in Table 27.

TABLE 27

Results from Washing and Pressing Pectin Waste Material

| Sample | Waste Kg | IPA Kg | IPA Density % | Waste Dry Matter % |
|---|---|---|---|---|
| 1151-105-0 | 20.0 | | | 16.8 |
| 1151-105-F1 | 9.5 | 42.1 | 30 | 24.4 |
| 1151-105-F2 | 9.1 | 36.2 | 50 | 33.8 |
| 1151-105-F3 | 7.7 | 34.1 | 60 | 33.9 |
| 1151-105-F4 | 8.0 | 33.2 | 70 | 28.9 |
| 1151-105-F-press | 4.3 | 255 | 78 | 51.5 |

Thus, when using a four step countercurrent wash with isopropanol followed by a single pressing, a dry matter of the waste of about 50% was achieved. This makes the waste combustible with an assumed combustion value about the same as wood with about 50% dry matter.

Combustion value of pectin waste: 8 GJ/ton

Combustion value of natural gas: 39 GJ/1000 $m^3$

Thus, by using the such washed and pressed pectin waste, about 20% natural gas can be saved with a following reduction in $CO_2$ emission.

Example 16

Consecutive Washing and Pressing with Isopropanol of Pectin Waste in Pilot Plant In order to establish if the same dry matter of pectin waste would be provided through consecutive washing and pressing, pectin waste material was washed in 80% isopropanol for 20 minutes and subsequently pressed on screw press at a counter pressure of 4 bar.

The results are listed in Table 28.

TABLE 28

Dry Matter of Washed and Pressed Pectin Waste

| Sample | Comment | Waste Dry Matter % |
|---|---|---|
| H-41 - Pectin | Fresh waste | 12.6 |
| H-41 - Pectin | 1. wash and press | 50.4 |
| H-41 - Pectin | 2. wash and press | 52.7 |
| H-41 - Pectin | 3. wash and press | 53.3 |

The data in Table 28 indicates that a single wash with 80% isopropanol followed by a single pressing at 4 bar is enough to increase the dry matter of the pectin waste to above 50%.

Example 17

Pectin Waste Material Washed Once with Different Concentrations of Ethanol

In this experiment, pectin waste material was washed once with different concentrations of ethanol and subsequently pressed once with a screw press at 4 bar counter pressure.

The results are listed in Table 29.

TABLE 29

Dry Matter of Pectin Waste Washed with Different Concentrations of Ethanol

| Sample | Comment | Ethanol % | Waste Dry Matter % | Comment |
| --- | --- | --- | --- | --- |
| H-6 - Pectin | Fresh waste | 0 | 13.9 | |
| H-6 - Pectin | Wash and press | 40 | | Not pressable |
| H-6 - Pectin | Wash and press | 65 | 44.6 | |
| H-6 - Pectin | Wash and press | 73 | 40.6 | |

This data in Table 29 shows that a combustible waste material is produced when using a concentration of ethanol of at least about 60%.

Example 18

Carrageenan Waste Material Washed Once with Isopropanol and Ethanol

Carrageenan waste is another example of material containing a water binding polymer. Such waste is traditionally used as soil improvement. In this experiment, carrageenan waste material was washed with 40% isopropanol and pressed on screw press. Also, carrageenan waste material was washed with 60% ethanol and pressed on screw press.

Results are listed in Table 30.

TABLE 30

Dry Matter of Carrageenan Waste Washed with Isopropanol and Ethanol

| Sample | Comment | IPA % | Ethanol % | Waste Dry Matter % |
| --- | --- | --- | --- | --- |
| C-128 - Carrageenan | Fresh waste | 0 | 0 | 30.5 |
| C-128 - Carrageenan | Wash and press | 40 | 0 | 54.7 |
| C-128 - Carrageenan | Wash and press | 0 | 60 | 46.3 |

The data in Table 30 indicates that washing with isopropanol or ethanol and pressing carrageenan waste leads to a high dry matter in the waste making it combustible. Also, the results indicate that isopropanol can be used in lower concentrations than ethanol.

In summary, Examples 15-18 show that a process according to embodiments of the present invention can be utilized to increase dry matter of polysaccharide containing waste material to provide for a combustible material to save energy and to reduce $CO_2$ emission.

Example 19

Sugar Beet Waste Material Washed with Isopropanol

In this example, sugar beet waste obtained after extraction of sugar was used according to an embodiment of the present invention. The dry matter of the sugar beet waste was 28.0%, and in a first test, 15 kg. sugar beet waste was washed for 20 minutes with 30 liters 40% isopropanol. The washed sugar beet waste could not be pressed on the screw press used in the previous examples, and when pressed on a double screw press (Stord Bard), the dry matter reached 26.7%. Similarly, when the washed sugar beet waste was run through a conventional decanter, the dry matter of the resulting material reached 28.2%. Without being bound of theory, it is believed that the denser structure of sugar beet waste require higher concentrations of alcohol and probably longer washing times.

Consequently, a series of washings were performed using 15 kg sugar beet waste and 30 liters isopropanol in each series. Washing was conducted from 1 hour to 45 hours and dry matter of the resulting material was determined after being pressed once and twice on the screw press used in previous examples.

TABLE 31

Dry Matter of Washed and Pressed Sugar Beet Waste

| Washing Time Hours | No of Pressings | Dry Matter % | Dry Matter % |
| --- | --- | --- | --- |
| 45 | 1 | 48.3 | |
| 45 | 2 | | 48.3 |
| 24 | 1 | 47.9 | |
| 24 | 2 | | 52.2 |
| 12 | 1 | 48.5 | |
| 12 | 2 | | 51.1 |
| 6 | 1 | 46.4 | |
| 6 | 2 | | 50.3 |
| 3 | 1 | 45.5 | |
| 3 | 2 | | 46.8 |
| 1 | 1 | 49.7 | |
| 1 | 2 | | 51.1 |

The data in Table 31 shows that the dry matter increased to about 50% by weight of the beet waste material after washing in 80% by weight isopropanol for one hour, and that a second pressing increased the dry matter marginally. This example shows that when dealing with denser polysaccharide containing materials, washing with alcohol for a longer period than about 20-30 minutes may be necessary.

Example 20

Two Step Alcohol Wash and Pressing of Conventionally Water Washed Fresh Peel

In this example, about 20 kg juiced orange peel was first washed with 40 liters water at room temperature, and then processed according to Example 14 using ethanol for washing.

TABLE 32

Results from Two Step Alcohol Wash of Conventionally Water Washed Orange Peel

| Sample | Peel Kg | EtOH Kg | EtOH Density % | Peel Dry Matter % | Pectin Yield % |
| --- | --- | --- | --- | --- | --- |
| 1151-108-A0 | 18.4 | | | 30.1 | 11.3 |
| 1151-108-A3 | 19.3 | 24.5 | 52 | 23.5 | |
| 1151-108-A4 | 19.3 | 25.1 | 66 | 22.8 | |
| 1151-108-A-press | 4.7 | 37.6 | 66 | 52.9 | 29.0 |
| 1151-108-B0 | 19.7 | | | 24.6 | |
| 1151-108-B3 | 22.5 | 34.6 | 44 | 22.4 | |
| 1151-108-B4 | 20.9 | 26.8 | 64 | 21.68 | |
| 1151-108-B-press | 5.5 | 39.2 | 62 | 54.4 | 30.9 |
| 1151-108-C0 | 19.4 | | | 24.5 | |
| 1151-108-C3 | 21.1 | 36.4 | 43 | 22.5 | |
| 1151-108-C4 | 19.5 | 26.0 | 63 | 23.2 | |
| 1151-108-C-press | 5.0 | 38.8 | 60 | 53.3 | 29.8 |

Comparing with Table 26 of Example 14, it is indicated that a first conventional water wash resulted in lower peel dry matter and lower pectin yield. Without being bound of theory, this may be explained through a loss of pectin during the first conventional water wash.

Table 33 lists the laboratory analysis of the resulting pectin products.

TABLE 33

Analysis of Resulting Pectin Products

| Pectin | Residual Sugar % | IV dl/g | DE % | GA % | Clarity Cold % T | Clarity Hot % T | pH | CS + Ca$^{2+}$ cP | CS − Ca$^{2+}$ cP |
|---|---|---|---|---|---|---|---|---|---|
| 1151-108-0A | 39.0 | 4.379 | 66.9 | 83.2 | 83.7 | 84.9 | 3.28 | 153.5 | 12.6 |
| 1151-108-A-pres | 8.5 | 3.847 | 68.8 | 84.8 | 92.1 | 93.1 | 3.07 | 14.8 | 10.5 |
| 1151-108-B-pres | 7.7 | 4.498 | 68.7 | 83.2 | 85.1 | 86.0 | 3.24 | 21.4 | 12.5 |
| 1151-108-C-pres | 6.7 | 4.065 | 68.7 | 85.6 | 85.6 | 90.8 | 3.08 | 17.5 | 11.3 |

The data in Table 33 indicates that a pre-wash with water appears to have reduced residual sugar somewhat when compared with the four step alcohol wash in Example 13. Further, the molecular weight measured as intrinsic viscosity is lower than that in Table 13. Without being bound by theory, this may be due to dissolution of some high molecular weight pectin during the water wash. However, other features of the resulting pectin products are on par with those found in Example 13. Thus, a pre-wash with water has the advantage of further reducing the residual sugar in the peel, but suffers with respect to peel dry matter, pectin yield and molecular weight of resulting pectin product.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

We claim:

1. A process for dewatering a starting biomass material comprising a polysaccharide and water, the process comprising:
    wetting the starting biomass material with a wetting composition comprising an alcohol to form a biomass slurry;
    mechanically separating at least a first portion of the wetting composition, water, or a combination thereof from the biomass slurry to form a wetted biomass material; and
    mechanically separating at least a second portion of the wetting composition, water, or a combination thereof from the wetted biomass material to form a dewatered biomass material, the dewatered biomass material comprising dry matter in an amount greater than the starting biomass material,
    wherein the starting biomass material is selected from the group consisting of citrus peel, apple pomace, sugar beet residue from sugar production, sun flower residue from sun flower oil production, potato residue from starch production, red seaweed, and brown seaweed.

2. A process as in claim 1 further comprising extracting at least one biomass component from the biomass material before the wetting step.

3. A process as in claim 2 wherein the at least one biomass component comprises juice.

4. A process as in claim 1 further comprising comminuting the biomass material before the wetting step.

5. A process as in claim 1 wherein the wetting step comprises washing the biomass material with the wetting composition.

6. A process as in claim 1 wherein the wetting step comprises washing the biomass material with the wetting composition with a plurality of washings, and the step of mechanically separating at least a portion of the wetting composition, water, or a combination thereof from the biomass slurry comprises mechanically separating at least a portion of the wetting composition, water, or a combination thereof from the biomass slurry after each of the plurality of washings.

7. A process as in claim 6 wherein the plurality of washings comprise 2 to 4 washings.

8. A process as in claim 6 wherein the plurality of washings is conducted counter-currently.

9. A process as in claim 1 wherein the step of mechanically separating at least a portion of the wetting composition, water, or a combination thereof from the wetted biomass material comprises pressing the wetted biomass material.

10. A process as in claim 6 wherein the step of mechanically separating at least a portion of the wetting composition, water, or a combination thereof from the wetted biomass material comprises pressing the wetted biomass material.

11. A process as in claim 6 wherein the step of mechanically separating at least a portion of the wetting composition, water, or a combination thereof from the wetted biomass material comprises pressing the wetted biomass material after each of the plurality of washings.

12. A process as in claim 1 wherein the step of mechanically separating at least a portion of the water from the wetted biomass material is carried out such that the dewatered biomass material comprises dry matter in an amount from about 35 to about 60% by weight of the dewatered biomass material.

13. A process as in claim 1 wherein the step of mechanically separating at least a portion of the water from the wetted biomass material is carried out such that the dewatered biomass material comprises dry matter in an amount from about 45 to about 60% by weight of the dewatered biomass material.

14. A process as in claim 1 further comprising combusting at least a portion of the dewatered biomass material to produce heat and using the heat in the dewatering process or in other heating applications.

15. A process as in claim 1 further comprising drying the dewatered biomass material with heat after the step of mechanically separating at least a portion of the wetting composition, water, or combination thereof from the wetted biomass material to form a dried dewatered biomass material.

16. A process as in claim 15 further comprising combusting at least a portion of the dried dewatered biomass material to form heat and using the heat in the dewatering process.

17. A process as in claim 1 wherein the biomass material comprises orange peel.

18. A process as in claim 1 wherein the alcohol is ethanol, isopropanol, or a combination thereof.

19. A process as in claim 1 wherein the alcohol is present in the wetting composition in an amount from about 40 to about 85% by weight of the wetting composition.

20. A process as in claim 1 wherein the alcohol is present in the wetting composition in an amount of at least about 70% by weight of the wetting composition.

21. A process as in claim 1 wherein the wetting composition further comprises water.

22. A process for extracting a polysaccharide from a starting biomass material comprising the polysaccharide and water, the process comprising:
    wetting the starting biomass material with a wetting composition comprising an alcohol to form a biomass slurry;
    mechanically separating at least a first portion of the wetting composition, water, or a combination thereof from the biomass slurry to form a wetted biomass material;
    mechanically separating at least a second portion of the wetting composition, water, or a combination thereof from the wetted biomass material to form a dewatered biomass material; and
    extracting at least a portion of the polysaccharide from the dewatered biomass material,
    wherein the starting biomass material is selected from the group consisting of citrus peel, apple pomace, sugar beet residue from sugar production, sun flower residue from sun flower oil production, potato residue from starch production, red seaweed, and brown seaweed.

23. A process as in claim 22 further comprising drying the dewatered biomass material with heat after the step of mechanically separating at least a portion of the wetting composition, water, or a combination thereof from the wetted biomass material, but before the extraction step, to form a dried dewatered biomass material.

24. A process as in claim 22 wherein the steps of wetting and mechanically separating are conducted at first location, the polysaccharide extracting step is conducted at a second location remote from the first location, and the process further comprises transporting at least a portion of the dewatered biomass material from the first location to the second location.

* * * * *